(12) United States Patent
Tzeng et al.

(10) Patent No.: US 7,829,567 B2
(45) Date of Patent: Nov. 9, 2010

(54) IMINO-INDENO[1,2-C] QUINOLINE DERIVATIVES, THEIR PREPARATION PROCESSES, AND PHARMACEUTICAL COMPOSITIONS COMPRISING THE SAME

(75) Inventors: Cherng-Chyi Tzeng, Kaohsiung (TW);
Yeh-Long Chen, Kaohsiung (TW);
Chih-Hua Tseng, Tainan (TW);
Pei-Jung Lu, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 90 days.

(21) Appl. No.: 11/982,167

(22) Filed: Oct. 31, 2007

(65) Prior Publication Data

US 2009/0111987 A1 Apr. 30, 2009

(51) Int. Cl.
*A61K 31/473* (2006.01)
*A61K 31/496* (2006.01)
*C07D 221/18* (2006.01)

(52) U.S. Cl. ............... 514/253.02; 514/284; 544/361; 544/58.6; 544/121; 544/125; 544/333; 544/357; 544/405; 544/238; 546/61; 540/575

(58) Field of Classification Search ............ None
See application file for complete search history.

(56) References Cited

FOREIGN PATENT DOCUMENTS

JP 09-143166 6/1997

OTHER PUBLICATIONS

Borsche et al. Chemical Abstracts vol. 35, Abstract No. 117g-i, 118a-d (1941) Abstract for Justus Liebigs Annalen der Chemie vol. 544, pp. 272-279 (1940).*
Vippagunta et al. Advanced Drug Delivery Reviews, vol. 48, pp. 3-26 (2001).*

* cited by examiner

*Primary Examiner*—Emily Bernhardt
(74) *Attorney, Agent, or Firm*—Townsend and Townsend and Crew LLP

(57) ABSTRACT

Disclosed herein are novel imino-indeno[1,2-c]quinoline derivatives of formula (I):

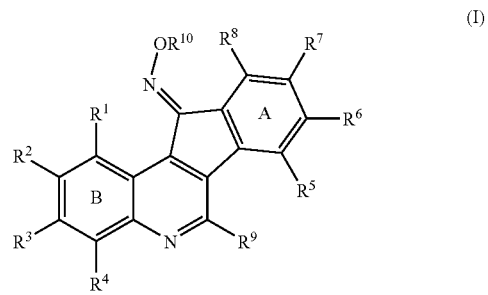

or a pharmaceutically acceptable salt or solvate thereof, wherein each of the substituents is given the definition as set forth in the Specification and Claims.

Also disclosed are the preparation processes of these derivatives, their synthetic precursors and their uses in the manufacture of pharmaceutical compositions for use in the treatment of cancers.

10 Claims, No Drawings

IMINO-INDENO[1,2-C] QUINOLINE DERIVATIVES, THEIR PREPARATION PROCESSES, AND PHARMACEUTICAL COMPOSITIONS COMPRISING THE SAME

BACKGROUND OF THE INVENTION

1. Field of the Invention

This invention relates to novel imino-indeno[1,2-c]quinoline derivatives, which have been proven to have a broad and potent anticancer activity. This invention also relates to processes for preparing these derivatives, as well as the uses of the same in the manufacture of pharmaceutical compositions.

2. Description of the Related Art

A number of indenoisoquinolines, especially indeno[1,2-c]isoquinoline derivatives, have been synthesized and proven to possess DNA topoisomerase I (top I) inhibitory activity. Their mechanism of action is identical to that of the natural alkaloid camptothecin and its clinically useful derivative topotecan. These compounds bind to a transient top I-DNA covalent complex and inhibit the resealing of a single-strand nick that the top I creates to relieve superhelical tension in duplex DNA.

Since indenoisoquinolines were discovered as a novel class of potential anticancer drug candidates, extensive structural modifications have been explored by altering the substituent(s) of the tetracyclic pharmacophore thereof. However, synthesis and evaluation of the isomeric indenoquinoline skeleton attract only very limited attention.

The quinoline ring constitutes a wide variety of biologically active compounds and is frequently condensed with various heterocycles. For example, furo[2,3-b]quinoline derivatives have been synthesized and demonstrated to possess anticancer activity.

JP 09143166 A2 discloses condensed indan derivatives of formula (2a), which could be prepared by the following scheme:

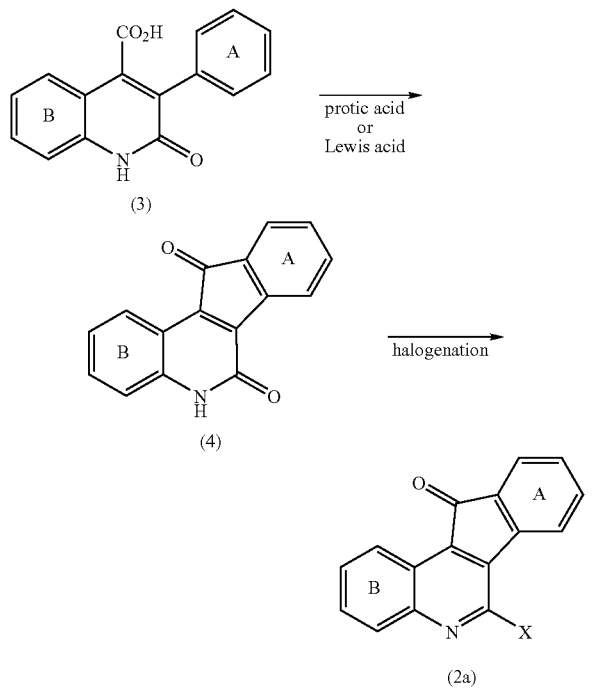

in which the starting compounds of formula (3), the A ring and B ring of which independently represent a benzene ring optionally substituted with one or more groups selected from a halogen atom, a lower alkyl, a lower alkoxy, hydroxy, nitro, an alkoxycarbonyl and a lower alkylenedioxy, could be prepared from 2-oxo-3-phenyl4-quinoline carboxylic acid derivatives according to the process reported in *Heterocyclic Chemistry*, 16:487-491 (1979), and X is a halogen atom.

The substituent X of the condensed indan derivatives of formula (2a) could be further modified to a substituent R, which corresponds to the substituent $R_1$ of formula (1) according to JP 09143166 A2 and which is defined to represent —$NR_3R_4$, an optionally substituted nitrogen-containing heterocyclic group or —$OR_5$, in which $R_3$ and $R_4$ are independently selected from hydrogen, phenyl, an optionally substituted nitrogen-containing heterocyclic group or a lower alkyl group optionally substituted with an amino group, a lower alkoxy group, phenyl, a nitrogen-containing heterocyclic group and hydroxy, and in which $R_5$ represents a lower alkyl group substituted with a substituted amino group.

However, the whole disclosure of JP 09143166 A2 only exemplifies the synthesis of the following compounds of formula (2a):

9-methoxy-6-[1-(4-methyl)piperazinyl]-11H-indeno[1,2-c]quinolin-11-one dihydrochloride (compound 1, in which R is 4-methyl-piperazinyl), 9-hydroxy-6-[1-(4-methyl)piperazinyl]-11H-indeno[1,2-c]quinolin-11-one dihydrochloride (compound 2, in which R is 4-methyl-piperazinyl), 9-methoxy-6N-[2-(dimethylamino)ethyl]amino-11H-indeno[1,2-c]quinolin-11-one dihydrochloride (compound 3, in which R is —$NHCH_2CH_2N(CH_3)_2$), 2,9-dimethoxy-6-[1-(4-methyl)piperazinyl]-11H-indeno[1,2-c]quinolin-11-one dihydrochloride (compound 4, in which R is 4-methyl-piperazinyl), and 2,9-dihydroxy-6-[1-(4-methyl)piperazinyl]-11H-indeno[1,2-c]quinolin-11-one dihydrochloride (compound 5, in which R is 4-methyl-piperazinyl).

In a previous study, the applicants synthesized certain indolo[2,3-b]quinoline derivatives and evaluated their anticancer activities on the ground that these tetracyclic heterocycles might intercalate into the DNA double helix, resulting in the inhibition of DNA replication and transcription.

In spite of the aforesaid, for pharmachemists and manufacturers in the Pharmaceutical Industry, there still exists a need to develop new compounds that can be easily prepared and that are suitable for use in the treatment of a variety of cancers and tumors.

SUMMARY OF THE INVENTION

Therefore, according to a first aspect, this invention provides a compound of formula (I):

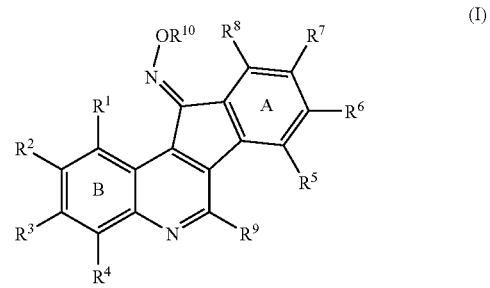

or a pharmaceutically acceptable salt or solvate thereof, wherein:
R¹, R², R³ and R⁴, which may be the same or different, independently represent:
(1) hydrogen, halogen, hydroxy, mercapto, cyano, nitro, —COOH, or —CONH₂;
(2) a group (i) selected from an amino group, a $C_1$-$C_{12}$ alkyl group, a $C_1$-$C_{12}$ alkoxy group, a $C_1$-$C_{12}$ alkoxycarbonyl group, a $C_1$-$C_{12}$ alkylthio group, a $C_1$-$C_{12}$ alkanoyl group, a $C_1$-$C_{12}$ alkanoyloxy group, a $C_2$-$C_{12}$ alkenyl group and a $C_2$-$C_{12}$ alkenoyl group, the group (i) being unsubstituted or substituted with one to three substituents selected from the group consisting of halo, amino, cyano, hydroxy, mercapto, —COOH, —CF₃, —OCF₃, —SCF₃, —CONH₂, a $C_1$-$C_6$ alkoxy group, and an aryl group; or
(3) a group (ii) selected from phenyl, phenoxy, phenylthio, pyridyl, pyrrolidinyl, piperazinyl, piperidyl and diazepinyl, the group (ii) being unsubstituted or substituted with one to three substituents selected from the group consisting of halo, amino, cyano, hydroxy, mercapto, —COOH, —CF₃, —OCF₃, —SCF₃, —CONH₂, a $C_1$-$C_{16}$ alkyl group, a $C_1$-$C_6$ alkoxy group, an aryl group, and a $C_3$-$C_{12}$ heterocyclic group containing one to three heteroatoms selected from O, S and N;
or two adjacent groups selected from R¹, R², R³ and R⁴ together form a ($C_1$-$C_6$)alkylenedioxy group or a ($C_1$-$C_6$)alkylene group;
or two adjacent groups selected from R¹, R², R³ and R⁴ together with the carbon atoms to which they are attached form a benzene ring;
R⁵, R⁶, R⁷ and R⁸, which may be the same or different, independently represent:
(1) hydrogen, halogen, hydroxy, mercapto, cyano, nitro, —COOH, or —CONH₂;
(2) a group (i) selected from an amino group, a $C_1$-$C_{12}$ alkyl group, a $C_1$-$C_{12}$ alkoxy group, a $C_1$-$C_{12}$ alkoxycarbonyl group, a $C_1$-$C_{12}$ alkylthio group, a $C_1$-$C_{12}$ alkanoyl group, a $C_1$-$C_{12}$ alkanoyloxy group, a $C_2$-$C_{12}$ alkenyl group and a $C_2$-$C_{12}$ alkenoyl group, the group (i) being unsubstituted or substituted with one to three substituents selected from the group consisting of halo, amino, cyano, hydroxy, mercapto, —COOH, —CF₃, —OCF₃, —SCF₃, —CONH₂, a $C_1$-$C_6$ alkoxy group, and an aryl group; or
(3) a group (ii) selected from phenyl, phenoxy, phenylthio, pyridyl, pyrrolidinyl, piperazinyl, piperidyl and diazepinyl, the group (ii) being unsubstituted or substituted with one to three substituents selected from the group consisting of halo, amino, cyano, hydroxy, mercapto, —COOH, —CF₃, —OCF₃, —SCF₃, —CONH₂, a $C_1$-$C_6$ alkyl group, a $C_1$-$C_6$ alkoxy group, an aryl group, and a $C_3$-$C_{12}$ heterocyclic group containing one to three heteroatoms selected from O, S and N;
or two adjacent groups selected from R⁵, R⁶, R⁷ and R⁸ together form a ($C_1$-$C_6$)alkylenedioxy group or a ($C_1$-$C_6$)alkylene group;
or two adjacent groups selected from R⁵, R⁶, R⁷ and R⁸ together with the carbon atoms to which they are attached form a benzene ring;
R⁹ represents:
(1) hydrogen;
(2) halogen;
(3) hydroxy;
(4) a $C_1$-$C_6$ alkoxy group which is unsubstituted or substituted with one to three substituents selected from the group consisting of halo, amino, cyano, hydroxy, mercapto, —COOH, —CF₃, —OCF₃, —SCF₃, —CONH₂, a $C_1$-$C_6$ alkyl group, a $C_1$-$C_6$ alkoxy group, an aryl group, and a $C_3$-$C_{12}$ heterocyclic group containing one to three heteroatoms selected from O, S and N;
(5) a nitrogen-containing heterocyclic group unsubstituted or substituted with one to three substituent groups selected from a $C_1$-$C_6$ alkyl group, a $C_1$-$C_6$ alkanoyl group, and a $C_1$-$C_{20}$ alkanoyl group interrupted by one or two amino groups of formula —NR'— where R' is hydrogen or ($C_1$-$C_6$)alkyl, each of the substituent groups being unsubstituted or substituted with one to three groups selected from halo, amino, cyano, hydroxy, mercapto, —COOH, —CONH₂, a $C_1$-$C_6$ alkyl group, a $C_1$-$C_6$ alkoxy group, a ($C_1$-$C_6$)alkylamino group, a ($C_1$-$C_6$)dialkylamino group, an aryl group, and a $C_3$-$C_{12}$ heterocyclic group containing one to three heteroatoms selected from O, S and N; or
(6) a group of formula —NHR, in which R represents: a $C_1$-$C_6$ alkyl group, an aryl group, a $C_3$-$C_{12}$ heterocyclic group containing one to three heteroatoms selected from O, S and N, or a $C_1$-$C_{20}$ alkyl group interrupted by one or two amino groups of formula —NR'— where R' is hydrogen or ($C_1$-$C_6$)alkyl, and wherein R is unsubstituted or substituted with one to three substituents selected from halo, amino, cyano, hydroxy, mercapto, —COOH, —CONH₂, a $C_1$-$C_6$ alkyl group, a $C_1$-$C_6$ alkoxy group, a $C_1$-$C_6$ alkanoyl group, a ($C_1$-$C_6$)alkylamino group, a ($C_1$-$C_6$)dialkylamino group, an aryl group, and a $C_3$-$C_{12}$ heterocyclic group containing one to three heteroatoms selected from O, S and N; and $R^{10}$ represents: hydrogen; or a group (iii) selected from a $C_1$-$C_6$ alkyl group, a $C_1$-$C_6$ aminoalkyl group, an aryl group, or a $C_3$-$C_{12}$ heterocyclic group containing one to three heteroatoms selected from O, S and N, the group (iii) being unsubstituted or substituted with one to three substituents selected from halo, amino, cyano, hydroxy, mercapto, —COOH, —CONH₂, a $C_1$-$C_6$alkyl group, a $C_1$-$C_6$ alkoxy group, a $C_1$-$C_6$ aminoalkyl group, an aryl group, and a $C_3$-$C_{12}$ heterocyclic group containing one to three heteroatoms selected from O, S and N.

In a second aspect, this invention provides a process for preparing a compound of formula (I), comprising subjecting a compound of formula (II):

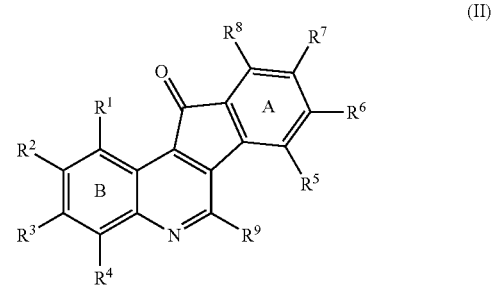

(II)

wherein the R¹-R⁹ groups have the same definitions as those defined for the compound of formula (I) described above, to a chemical treatment selected from:
(i) a reaction with $NH_2OH$, optionally followed by alkylation with an alkyl halide of formula $R^{10}X$, where $R^{10}$ has the same definition as that defined for the compound of formula (I) described above, and X is a halogen; and
(ii) a reaction with $NH_2OR^{10}$, where $R^{10}$ has the same definition as that defined for the compound of formula (I) described above.

In a third aspect, this invention provides a pharmaceutical composition comprising a compound of formula (I) or a pharmaceutically acceptable salt or solvate thereof as described above.

In a fourth aspect, this invention provides a method of treating a subject having a cancer disease comprising administering to the subject a compound of formula (I) or a pharmaceutically acceptable salt or solvate thereof as described above.

In a fifth aspect, this invention provides a process for preparing a compound of formula (III),

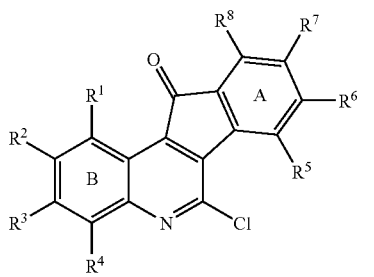

(III)

wherein the $R^1$-$R^8$ groups have the same definitions as those defined for the compound of formula (I) described above, the process comprising reacting a compound of formula (IV) with $POCl_3$:

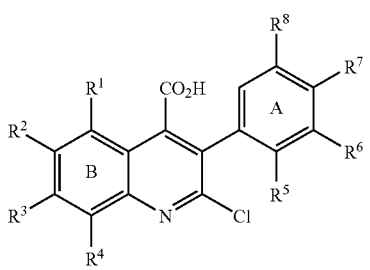

(IV)

wherein the $R^1$-$R^8$ groups have the same definitions as those defined for the compound of formula (I) described above.

DETAILED DESCRIPTION OF THE INVENTION

For the purpose of this specification, it will be clearly understood that the word "comprising" means "including but not limited to", and that the word "comprises" has a corresponding meaning.

It is to be understood that, if any prior art publication is referred to herein, such reference does not constitute an admission that the publication forms a part of the common general knowledge in the art, in Taiwan or any other country.

Unless defined otherwise, all technical and scientific terms used herein have the meaning commonly understood by a person skilled in the art to which this invention belongs. One skilled in the art will recognize many methods and materials similar or equivalent to those described herein, which could be used in the practice of the present invention. Indeed, the present invention is in no way limited to the methods and materials described. For clarity, the following definitions are used herein.

This invention provides imino-indeno[1,2-c]quinoline derivatives of formula (I):

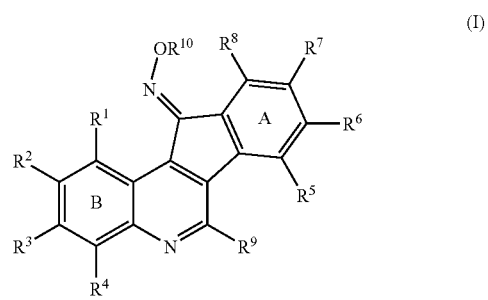

(I)

or a pharmaceutically acceptable salt or solvate thereof, wherein:

$R^1$, $R^2$, $R^3$ and $R^4$, which may be the same or different, independently represent:

(1) hydrogen, halogen, hydroxy, mercapto, cyano, nitro, —COOH, or —CONH$_2$;

(2) a group (i) selected from an amino group, a $C_1$-$C_{12}$ alkyl group, a $C_1$-$C_{12}$ alkoxy group, a $C_1$-$C_{12}$ alkoxycarbonyl group, a $C_1$-$C_{12}$ alkylthio group, a $C_1$-$C_{12}$ alkanoyl group, a $C_1$-$C_{12}$ alkanoyloxy group, a $C_2$-$C_{12}$ alkenyl group and a $C_2$-$C_{12}$ alkenoyl group, the group (i) being unsubstituted or substituted with one to three substituents selected from the group consisting of halo, amino, cyano, hydroxy, mercapto, —COOH, —CF$_3$, —OCF$_3$, —SCF$_3$, —CONH$_2$, a $C_1$-$C_6$ alkoxy group, and an aryl group; or (3) a group (ii) selected from phenyl, phenoxy, phenylthio, pyridyl, pyrrolidinyl, piperazinyl, piperidyl and diazepinyl, the group (ii) being unsubstituted or substituted with one to three substituents selected from the group consisting of halo, amino, cyano, hydroxy, mercapto, —COOH, —CF$_3$, —OCF$_3$, —SCF$_3$, —CONH$_2$, a $C_1$-$C_6$ alkyl group, a $C_1$-$C_6$ alkoxy group, an aryl group, and a $C_3$-$C_{12}$ heterocyclic group containing one to three heteroatoms selected from O, S and N;

or two adjacent groups selected from $R^1$, $R^2$, $R^3$ and $R^4$ together form a ($C_1$-$C_6$)alkylenedioxy group or a ($C_1$-$C_6$)alkylene group;

or two adjacent groups selected from $R^1$, $R^2$, $R^3$ and $R^4$ together with the carbon atoms to which they are attached form a benzene ring;

$R^5$, $R^6$, $R^7$ and $R^8$, which may be the same or different, independently represent:

(1) hydrogen, halogen, hydroxy, mercapto, cyano, nitro, —COOH, or —CONH$_2$;

(2) a group (i) selected from an amino group, a $C_1$-$C_{12}$ alkyl group, a $C_1$-$C_{12}$ alkoxy group, a $C_1$-$C_{12}$ alkoxycarbonyl group, a $C_1$-$C_{12}$ alkylthio group, a $C_1$-$C_{12}$ alkanoyl group, a $C_1$-$C_{12}$ alkanoyloxy group, a $C_2$-$C_{12}$ alkenyl group and a $C_2$-$C_{12}$ alkenoyl group, the group (i) being unsubstituted or substituted with one to three substituents selected from the group consisting of halo, amino, cyano, hydroxy, mercapto, —COOH, —CF$_3$, —OCF$_3$, —SCF$_3$, —CONH$_2$, a $C_1$-$C_6$ alkoxy group, and an aryl group; or (3) a group (ii) selected from phenyl, phenoxy, phenylthio, pyridyl, pyrrolidinyl, piperazinyl, piperidyl and diazepinyl, the group (ii) being unsubstituted or substituted with one to three substituents selected from the group consisting of halo, amino, cyano, hydroxy, mercapto, —COOH, —CF$_3$, —OCF$_3$, —SCF$_3$, —CONH$_2$, a $C_1$-$C_6$ alkyl group, a $C_1$-$C_6$ alkoxy group, an aryl group, and a $C_3$-$C_{12}$ heterocyclic group containing one to three heteroatoms selected from O, S and N;

or two adjacent groups selected from $R^5$, $R^6$, $R^7$ and $R^8$ together form a ($C_1$-$C_6$)alkylenedioxy group or a ($C_1$-$C_6$)alkylene group;

or two adjacent groups selected from $R^5$, $R^6$, $R^7$ and $R^8$ together with the carbon atoms to which they are attached form a benzene ring;

$R^9$ represents:
(1) hydrogen;
(2) halogen;
(3) hydroxy;
(4) a $C_1$-$C_6$ alkoxy group which is unsubstituted or substituted with one to three substituents selected from the group consisting of halo, amino, cyano, hydroxy, mercapto, —COOH, —CF$_3$, —OCF$_3$, —SCF$_3$, —CONH$_2$, a $C_1$-$C_6$ alkyl group, a $C_1$-$C_6$ alkoxy group, an aryl group, and a $C_3$-$C_{12}$ heterocyclic group containing one to three heteroatoms selected from O, S and N;
(5) a nitrogen-containing heterocyclic group unsubstituted or substituted with one to three substituent groups selected from a $C_1$-$C_6$ alkyl group, a $C_1$-$C_6$ alkanoyl group, and a $C_1$-$C_{20}$ alkanoyl group interrupted by one or two amino groups of formula —NR'— where R' is hydrogen or ($C_1$-$C_6$)alkyl, each of the substituent groups being unsubstituted or substituted with one to three groups selected from halo, amino, cyano, hydroxy, mercapto, —COOH, —CONH$_2$, a $C_1$-$C_6$ alkyl group, a $C_1$-$C_6$ alkoxy group, a ($C_1$-$C_6$)alkylamino group, a ($C_1$-$C_6$)dialkylamino group, an aryl group, and a $C_3$-$C_{12}$ heterocyclic group containing one to three heteroatoms selected from O, S and N; or
(6) a group of formula —NHR, in which R represents: a $C_1$-$C_6$ alkyl group, an aryl group, a $C_3$-$C_{12}$ heterocyclic group containing one to three heteroatoms selected from O, S and N, or a $C_1$-$C_{20}$ alkyl group interrupted by one or two amino groups of formula —NR'— where R' is hydrogen or ($C_1$-$C_6$)alkyl, and wherein R is unsubstituted or substituted with one to three substituents selected from halo, amino, cyano, hydroxy, mercapto, —COOH, —CONH$_2$, a $C_1$-$C_6$ alkyl group, a $C_1$-$C_6$ alkoxy group, a $C_1$-$C_6$ alkanoyl group, a ($C_1$-$C_6$)alkylamino group, a ($C_1$-$C_6$)dialkylamino group, an aryl group, and a $C_3$-$C_{12}$ heterocyclic group containing one to three heteroatoms selected from O, S and N; and $R^{10}$ represents: hydrogen; or a group (iii) selected from a $C_1$-$C_6$ alkyl group, a $C_1$-$C_6$ aminoalkyl group, an aryl group, or a $C_3$-$C_{12}$ heterocyclic group containing one to three heteroatoms selected from O, S and N, the group (iii) being unsubstituted or substituted with one to three substituents selected from halo, amino, cyano, hydroxy, mercapto, —COOH, —CONH$_2$, a $C_1$-$C_6$ alkyl group, a $C_1$-$C_6$ alkoxy group, a $C_1$-$C_6$ aminoalkyl group, an aryl group, and a $C_3$-$C_{12}$ heterocyclic group containing one to three heteroatoms selected from O, S and N.

According to this invention, the term "halogen" or the term "halo" as used herein inter alia refers to fluoro, chloro, bromo and iodo.

Unless otherwise indicated, the term "alkyl group" as used herein alone or as part of another group includes both straight- and branched-chain hydrocarbons containing in the normal chain 1 to 12 carbons, preferably 1 to 6 carbons, and may be unsubstituted or substituted with one to three substituents as described for the $R^1$ to $R^{10}$ groups wherever appropriate. Preferably, the term "alkyl group" as used herein alone or as part of another group includes, but is not limited to, methyl, ethyl, propyl, isopropyl, n-butyl, isobutyl, sec-butyl, tert-butyl, n-pentyl, isopentyl, neopentyl, n-hexyl, isohexyl, heptyl, isoheptyl, octyl, nonyl, decyl, undecyl, dodecyl, the various branched chain isomers thereof, etc.

The alkoxy group includes, for example, straight- or branched-chain alkoxy groups, such as methoxy, ethoxy, n-propoxy, isopropoxy, n-butoxy, isobutoxy, sec-butoxy, tert-butoxy, pentyloxy, hexyloxy, etc.

The alkanoyloxy group includes straight- or branched-chain alkanoyloxy groups, such as formyloxy, acetoxy, propionyloxy, butyryloxy, 2-methylpropionyloxy, pivaloyloxy, pentanoyloxy, 3-methylbutyryloxy, hexanoyloxy, etc.

The lower alkoxycarbonyl group includes straight- or branched-chain alkoxycarbonyl groups, such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, pentyloxycarbonyl, hexyloxycarbonyl, etc.

The alkyl group which has substituted amino group(s) includes, for example, mono- or di-alkylaminoalkyl groups wherein the alkyl moiety has 1 to 6 carbon atoms, such as methylaminomethyl, ethylaminomethyl, methylaminoethyl, ethylaminoethyl, dimethylaminomethyl, dimethylaminoethyl, dimethylaminopropyl, diethylaminomethyl, diethylaminoethyl, diethylaminopropyl, diethylaminobutyl, diethylaminopenta-2-yl, dipropylaminoethyl, dibutylaminoethyl, dibutylaminohexyl, etc.

The alkyl group which has substituted alkoxy group(s) includes straight- or branched-chain alkyl groups substituted by a $C_1$-$C_6$ alkoxy group, such as methoxymethyl, ethoxymethyl, propoxymethyl, methoxyethyl, ethoxyethyl, methoxypropyl, etc.

Unless otherwise indicated, the term "alkylene" as used herein or as part of another group refers to an alkyl linking group having single bonds for attachment to other groups at two different carbon atoms, such as methylene, ethylene, propylene, 1,4-butylene, and the like.

Unless otherwise indicated, the term "alkenyl" as used herein by itself or as part of another group refers to straight- or branched-chain radicals of 2 to 12 carbons, preferably 2 to 6 carbons, in the normal chain, which include one or more double bonds in the normal chain, such as, for example, vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, etc.

According to this invention, the term "aryl group" as used herein by itself or as part of another group includes, but is not limited to, phenyl, tolyl, xylyl, naphthyl, anthryl, phenanthryl, etc., each of which may be unsubstituted or substituted with one to three substituents as described for the $R^1$ to $R^{10}$ groups.

According to this invention, the term "heterocyclic group" as used herein includes, but is not limited to, oxiranyl, oxetanyl, aziridinyl, azetidinyl, furyl, tetrahydrofuryl, pyrrolyl, pyrrolidinyl, pyrrolinyl, thienyl, imidazolyl, pyrazolyl, pyrazolinyl, pyrazolidinyl, triazolyl, oxazolyl, isoxazolyl, thiazolyl, isothiazolyl, pyranyl, pyridyl, piperidyl, piperazinyl, morpholinyl, pyrazinyl, pyrimidinyl, pyridazinyl, diazepinyl, thiazinyl, indolyl, isoindolyl, indolinyl, isoindolinyl, indazolyl, benzofuryl, isobenzofuryl, benzothienyl, benzimidazolyl, benzoxazolyl, benzisoxazolyl, benzothiazolyl, quinolyl, isoquinolyl, quinoxalinyl, quinazolinyl, acridinyl, cinnolinyl, dioxanyl, uracilyl, purinyl, etc., each of which may be unsubstituted or substituted with one to three substituents as described for the $R^1$ to $R^{10}$ groups.

According to this invention, the term "nitrogen-containing heterocyclic group" as used herein includes, but is not limited to, aziridinyl, azetidinyl, pyrrolyl, pyrrolinyl, pyrrolidinyl, pyrazolyl, pyrazolinyl, pyrazolidinyl, imidazolyl, triazolyl, oxazolyl, isoxazolyl, thiazolyl, isothiazolyl, pyridyl, piperidyl, pyridazinyl, pyrimidinyl, pyrazinyl, piperazinyl, morpholinyl, diazepinyl, thiazinyl, indolyl, isoindolyl, indolinyl, isoindolinyl, indazolyl, benzimidazolyl, benzoxazolyl, benzisoxazolyl, benzothiazolyl, quinolyl, isoquinolyl, quinoxalinyl, quinazolinyl, acridinyl, cinnolinyl, purinyl, dioxanyl, uracilyl, etc., each of which may be unsubstituted or substituted with one to three substituents as described for the $R^1$ to $R^{10}$ groups.

Preferably, $R^1$, $R^2$, $R^3$ and $R^4$ independently represent: hydrogen, halogen, hydroxy, mercapto, cyano, nitro, —COOH or —CONH$_2$; or a group (i) selected from an amino group, a $C_1$-$C_6$ alkyl group, a $C_1$-$C_6$ alkoxy group, a $C_1$-$C_6$ alkoxycarbonyl group, a $C_1$-$C_6$ alkylthio group, a $C_1$-$C_6$ alkanoyl group, a $C_1$-$C_6$ alkanoyloxy group, a $C_2$-$C_6$ alkenyl group and a $C_2$-$C_6$ alkenoyl group, the group (i) being unsubstituted or substituted with one to three substituents selected from the group consisting of halo, amino, cyano, hydroxy, mercapto, —COOH, —CF$_3$, —OCF$_3$, —SCF$_3$, —CONH$_2$, a $C_1$-$C_6$ alkoxy group, and phenyl; or a group (ii) selected from phenyl, phenoxy, phenylthio, pyridyl, pyrrolidinyl, piperazinyl, piperidyl and diazepinyl, the group (ii) being unsubstituted or substituted with one to three substituents selected from the group consisting of halo, amino, cyano, hydroxy, mercapto, —COOH, —CF$_3$, —OCF$_3$, —SCF$_3$, —CONH$_2$, a $C_1$-$C_6$ alkyl group, a $C_1$-$C_6$ alkoxy group and a phenyl group.

More preferably, $R^1$, $R^2$, $R^3$ and $R^4$ independently represent: hydrogen, fluoro, chloro, bromo, iodo, hydroxy, mercapto, cyano, amino, nitro, —COOH, —CONH$_2$, methyl, ethyl, propyl, isopropyl, n-butyl, t-butyl, n-pentyl, methoxy, ethoxy, propoxy, butoxy, methylthio, ethylthio, formyl, acetyl, propionyl, butyryl, acetoxy, propionyloxy, butyryloxy, phenylacetyl, hydroxymethyl, aminomethyl, aminoethyl, fluoromethyl, chloromethyl, bromomethyl, trifluoromethyl, trifluoromethoxy, trifluoromethylthio, methoxycarbonyl, ethoxycarbonyl, propoxycarbonyl, butoxycarbonyl, phenyl, phenoxy, 4-hydroxy-3-isopropylphenoxy, phenylthio, benzyl, benzoyl, benzyloxy, styryl, anilino, 2,6-dichloroanilino, or 3-methylbuten-2-yl.

Alternatively, according to this invention, two adjacent groups selected from $R^1$, $R^2$, $R^3$ and $R^4$ together may form a ($C_1$-$C_6$)alkylenedioxy group, such as a methylenedioxy group. In a preferred embodiment of this invention, $R^1$ and $R^2$ together form a methylenedioxy group. In another preferred embodiment of this invention, $R^2$ and $R^3$ together form a methylenedioxy group. In a further preferred embodiment of this invention, $R^3$ and $R^4$ together form a methylenedioxy group.

Alternatively, according to this invention, two adjacent groups selected from $R^1$, $R^2$, $R^3$ and $R^4$ together may form a ($C_1$-$C_6$)alkylene group, such as a propylene group. In a preferred embodiment of this invention, $R^1$ and $R^2$ together form a propylene group. In another preferred embodiment of this invention, $R^2$ and $R^3$ together form a propylene group. In a further preferred embodiment of this invention, $R^3$ and $R^4$ together form a propylene group.

Alternatively, according to this invention, two adjacent groups selected from $R^1$, $R^2$, $R^3$ and $R^4$ together with the carbon atoms to which they are attached form a benzene ring. In a preferred embodiment of this invention, $R^1$ and $R^2$ together with the carbon atoms to which they are attached form a benzene ring. In another preferred embodiment of this invention, $R^2$ and $R^3$ together with the carbon atoms to which they are attached form a benzene ring. In a further preferred embodiment of this invention, $R^3$ and $R^4$ together with the carbon atoms to which they are attached form a benzene ring.

Preferably, $R^5$, $R^6$, $R^7$ and $R^8$ independently represent: hydrogen, halogen, hydroxy, mercapto, cyano, nitro, —COOH or —CONH$_2$, or a group (i) selected from an amino group, a $C_1$-$C_6$ alkyl group, a $C_1$-$C_6$ alkoxy group, a $C_1$-$C_6$ alkoxycarbonyl group, a $C_1$-$C_6$ alkylthio group, a $C_1$-$C_6$ alkanoyl group, a $C_1$-$C_6$ alkanoyloxy group, a $C_2$-$C_6$ alkenyl group and a $C_2$-$C_6$ alkenoyl group, the group (i) being unsubstituted or substituted with one to three substituents selected from the group consisting of halo, amino, cyano, hydroxy, mercapto, —COOH, —CF$_3$, —OCF$_3$, —SCF$_3$, —CONH$_2$, a $C_1$-$C_6$ alkoxy group, and phenyl; or a group (ii) selected from phenyl, phenoxy, phenylthio, pyridyl, pyrrolidinyl, piperazinyl, piperidyl and diazepinyl, the group (ii) being unsubstituted or substituted with one to three substituents selected from the group consisting of halo, amino, cyano, hydroxy, mercapto, —COOH, —CF$_3$, —OCF$_3$, —SCF$_3$, —CONH$_2$, a $C_1$-$C_6$ alkyl group, a $C_1$-$C_6$ alkoxy group and a phenyl group.

More preferably, $R^5$, $R^6$, $R^7$ and $R^8$ independently represent: hydrogen, fluoro, chloro, bromo, iodo, hydroxy, mercapto, cyano, amino, nitro, —COOH, —CONH$_2$, methyl, ethyl, propyl, isopropyl, n-butyl, t-butyl, n-pentyl, methoxy, ethoxy, propoxy, butoxy, methylthio, ethylthio, formyl, acetyl, propionyl, butyryl, acetoxy, propionyloxy, butyryloxy, phenylacetyl, hydroxymethyl, aminomethyl, aminoethyl, fluoromethyl, chloromethyl, bromomethyl, trifluoromethyl, trifluoromethoxy, trifluoromethylthio, methoxycarbonyl, ethoxycarbonyl, propoxycarbonyl, butoxycarbonyl, phenyl, phenoxy, phenylthio, benzyl, benzoyl, benzyloxy, styryl, anilino, 4-hydroxy-3-isopropylphenoxy, or 2,6-dichloroanilino.

Alternatively, according to this invention, two adjacent groups selected from $R^5$, $R^6$, $R^7$ and $R^8$ together may form a ($C_1$-$C_6$)alkylenedioxy group, such as a methylenedioxy group. In a preferred embodiment of this invention, $R^5$ and $R^6$ together form a methylenedioxy group. In another preferred embodiment of this invention, $R^6$ and $R^7$ together form a methylenedioxy group. In a further preferred embodiment of this invention, $R^7$ and $R^8$ together form a methylenedioxy group.

Alternatively, according to this invention, two adjacent groups selected from $R^5$, $R^6$, $R^7$ and $R^8$ together with the carbon atoms to which they are attached form a benzene ring. In a preferred embodiment of this invention, $R^5$ and $R^6$ together form with the carbon atoms to which they are attached form a benzene ring. In another preferred embodiment of this invention, $R^6$ and $R^7$ together form with the carbon atoms to which they are attached form a benzene ring. In a further preferred embodiment of this invention, $R^7$ and $R^8$ together form with the carbon atoms to which they are attached form a benzene ring.

In the compound of formula (I) according to this invention, $R^9$ is preferably a nitrogen-containing heterocyclic group, which is selected from pyrrolyl, pyrrolinyl, pyrrolidinyl, pyrazolyl, pyrazolinyl, pyrazolidinyl, imidazolyl, triazolyl, oxazolyl, isoxazolyl, thiazolyl, isothiazolyl, pyridyl, piperidyl, pyridazinyl, pyrimidinyl, pyrazinyl, piperazinyl, morpholinyl, diazepinyl, thiazinyl, indolyl, isoindolyl, indolinyl, isoindolinyl, indazolyl, benzimidazolyl, benzoxazolyl, benzisoxazolyl, benzothiazolyl, quinolyl, isoquinolyl, quinoxalinyl, quinazolinyl, acridinyl, cinnolinyl, purinyl, dioxanyl and uracilyl, and which is unsubstituted or substituted with one to three substituent groups selected from a $C_1$-$C_6$ alkyl group, a $C_1$-$C_6$ alkanoyl group, and a $C_1$-$C_{20}$ alkanoyl group interrupted by one or two amino groups of formula —NR'— where R' is hydrogen or ($C_1$-$C_6$)alkyl, each of the substituent groups being unsubstituted or substituted with one to three groups selected from halo, amino, cyano, hydroxy, mercapto, —COOH, —CONH$_2$, a $C_1$-$C_6$ alkyl group, a $C_1$-$C_6$ alkoxy group, a ($C_1$-$C_6$)alkylamino group, a ($C_1$-$C_6$)dialkylamino group, phenyl, oxiranyl, pyridyl, pyrrolidinyl, piperidyl, piperazinyl, diazepinyl, and morpholinyl.

Alternatively, in the compound of formula (I) according to this invention, $R^9$ is preferably a group of formula —NHR, in which R represents: phenyl, a $C_1$-$C_6$ alkyl group, or a $C_1$-$C_{20}$ alkyl group interrupted by one or two amino groups of formula —NR'— where R' is hydrogen or ($C_1$-$C_6$)alkyl, and wherein R is unsubstituted or substituted with one to three substituents selected from halo, amino, cyano, hydroxy, mercapto, —COOH, —CONH$_2$, a $C_1$-$C_6$ alkyl group, a $C_1$-$C_6$ alkoxy group, a $C_1$-$C_6$ alkanoyl group, a ($C_1$-$C_6$)alkylamino group, a ($C_1$-$C_6$)dialkylamino group, phenyl, oxiranyl, pyridyl, pyrrolidinyl, piperidyl, piperazinyl, diazepinyl, and morpholinyl.

Preferably, the $C_1$-$C_{20}$ alkanoyl group interrupted by one or two amino groups of formula —NR'— includes: groups represented by the formula —CO(CH$_2$)$_m$NR'(CH$_2$)$_n$R", in which R' is hydrogen or ($C_1$-$C_6$)alkyl, R" is halo, hydroxy, —NH$_2$, —NH($C_1$-$C_6$)alkyl or —N($C_1$-$C_6$)dialkyl, and m and n independently are an integer of 1-6; and groups represented by the formula —CO(CH$_2$)$_a$NR'(CH$_2$)$_b$NR'(CH$_2$)$_c$R", in which R' in each occurrence is hydrogen or ($C_1$-$C_6$)alkyl, R" is halo, hydroxy, —NH$_2$, —NH($C_1$-$C_6$)alkyl or —N($C_1$-$C_6$)dialkyl, and a, b and c independently are an integer of 1-6.

Representative examples of the $R^9$ group include, but are not limited to: hydrogen, chloro, hydroxy; methoxy, ethoxy, methoxyamino, 2-ethoxyethylamino, 4-aminopiperidyl, 3-(dimethylamino)propylamino, 2-aminopyrrolidinyl, 3-acetylphenylamino, 3-methoxyphenylamino, 4-fluorophenylamino, 4-chlorophenylamino, 2-(dimethylamino)ethylamino, 2-acetylphenylamino, 2,4-difluorophenylamino, 4-acetylphenylamino, 1,4-diazepin-1-yl, 3,4-difluorophenylamino, 2,4-dichlorophenylamino, 4-methoxyphenylamino, piperazin-1-yl, 2,4-dimethoxyphenylamino, 2-(2-hydroxyethylamino)ethylamino, 4-(2-methylaminoacetyl)piperazin-1-yl, 4-(4-chlorobutyryl)piperazin-1-yl, 4-(3-chloropropionyl)piperazin-1-yl, 4-[2-(2-aminoethyl)aminoacetyl]piperazin-1-yl, 3-methylpiperazin-1-yl, 4-2-chloroacetyl)piperazin-1-yl, 4-(3-hydroxypropionyl)piperazin-1-yl, 4-(2-dimethylaminoacetyl)piperazin-1-yl, 3,4-dimethoxyphenylamino, 4-(2-hydroxyacetyl)piperazin-1-yl, 4-(4-dimethylaminobutyryl)piperazin-1-yl, 4-[(3-dimethylamino)propionyl]piperazin-1-yl, 4-[2-(2-hydroxyethyl)aminoacetyl]piperazin-1-yl, 4-(2-hydroxy-3-(methylamino)propyl)piperazin-1-yl, 4-[3-(2-hydroxyethylamino)propionyl]piperazin-1-yl, 4-[2-hydroxy-3-(dimethylamino)propyl]piperazin-1-yl, 4-{3-[2-(dimethylamino)ethylamino]propanoyl}piperazin-1-yl.

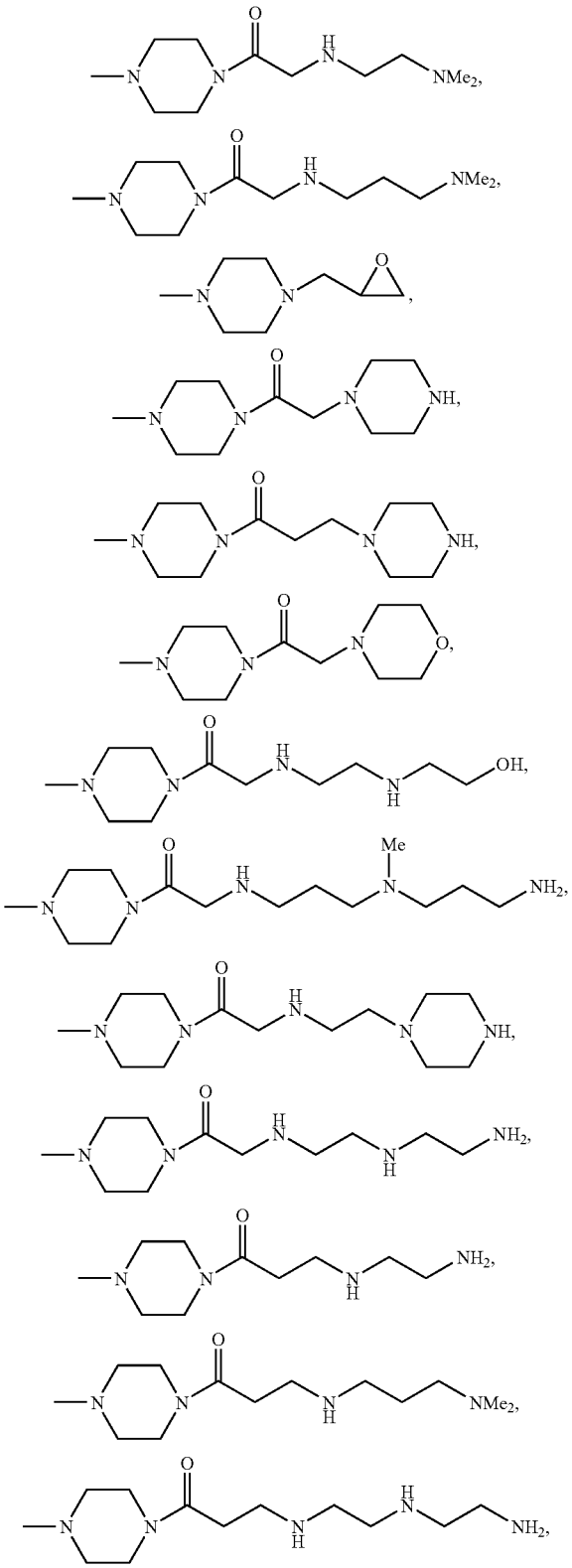

-continued

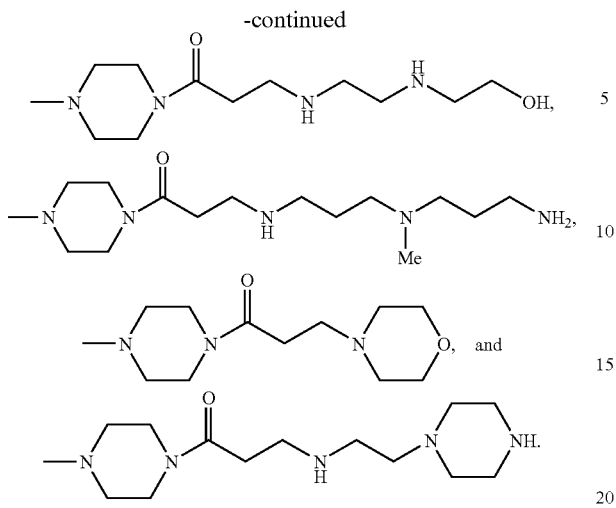

In the compound of formula (I) according to this invention, $R^{10}$ is preferably selected from: hydrogen; or a group (iii) selected from a $C_1$-$C_6$ alkyl group, a $C_1$-$C_6$ aminoalkyl group and phenyl, the group (iii) being unsubstituted or substituted with one to three substituents selected from halo, amino, cyano, hydroxy, mercapto, —COOH, —CONH$_2$, a $C_1$-$C_6$ alkyl group, a $C_1$-$C_6$ alkoxy group, a $C_1$-$C_6$ aminoalkyl group, phenyl, oxiranyl, pyridyl, pyrrolidinyl, piperidyl, piperazinyl, diazepinyl, and morpholinyl.

Representative examples of the $R^{10}$ group include, but are not limited to: hydrogen, methyl, benzyl, 3-aminopropyl, 2-(morpholin-1-yl)ethyl, oxiran-2-ylmethyl, 2-(pyrrolidin-1-yl)ethyl, 3-(dimethylamino)propyl, 2-dimethylamino)ethyl, 2-hydroxy-3-(dimethylamino)propyl, and 2-(piperidin-1-yl) ethyl.

Representative examples of compounds of formula (I) according to this invention include, but are not limited to:
9-methoxy-11H-indeno[1,2-c]quinolin-11-one oxime;
6-hydroxy-9-methoxy-11H-indeno[1,2-c]quinolin-11-one oxime;
6-(Piperazin-1-yl)-11H-indeno[1,2-c]quinolin-11-one O-methyl oxime;
3-[2-(Dimethylamino)ethylamino]-1-{4-[11-(hydroxy-imino)9-methoxy-11H-indeno[1,2-c]quinolin-6-yl]piperazin-1-yl}propan-1-one;
9-Methoxy-6-(piperazin-1-yl)-11H-indeno[1,2-c]quinolin-11-one oxime;
9-Methoxy-6-(piperazin-1-yl)-11H-indeno[1,2-c]quinolin-11-one O-2-(dimethylamino)ethyl oxime;
9-Methoxy-6-(piperazin-1-yl)-11H-indeno[1,2-c]quinolin-11-one O-3-(dimethylamino)propyl oxime;
9-Methoxy-6-piperazin-1-yl)-11H-indeno[1,2-c]quinolin-11-one O-3-aminopropyl oxime;
9-Methoxy-6-(piperazin-1-yl)-11H-indeno[1,2-c]quinolin-11-one O-2-(pyrrolidin-1-yl)ethyl oxime;
9-Methoxy-6-(piperazin-1-yl)-11H-indeno[1,2-c]quinolin-11-one O-2-(piperidin-1-yl)ethyl oxime;
9-Methoxy-11H-indeno[1,2-c]quinolin-11-one O-2-(pyrrolidin-1-yl)ethyl oxime; and
6-hydroxy-9-methoxy-11H-indeno[1,2-c]quinolin-11-one O-2-(pyrrolidin-1-yl)ethyl oxime.

This invention also provides a process for preparing a compound of formula (I) as described above, comprising subjecting a compound of formula (II):

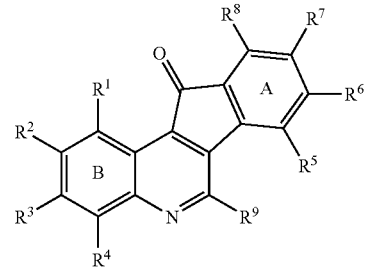

wherein the $R^1$-$R^9$ groups have the same definitions as those defined for the compound of formula (I) described above,
to a chemical treatment selected from:
(i) a reaction with NH$_2$OH, optionally followed by alkylation with an alkyl halide of formula $R^{10}$X, where $R^{10}$ the same definition as that defined for the compound of formula (I) described above, and X is a halogen; and
(ii) a reaction with NH$_2$O$R^{10}$, where $R^{10}$ has the same definition as that defined for the compound of formula (I) described above.

The preparation process of the compound of formula (I) according to this invention may be carried out in the presence of an appropriate solvent that favors the production of the compound of formula (I) from the selected chemical treatment, such as ethoxyethanol, DMF and so forth. In addition, the reaction advantageously proceeds under microwave irradiation.

The compound of formula (II) may be prepared by reacting a compound of formula (III):

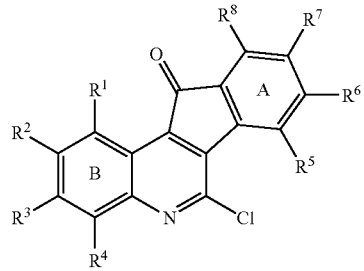

wherein the $R^1$-$R^8$ groups have the same definitions as those defined for the compound of formula (I) described above,
with a compound of formula $R^{9A}$H, where $R^{9A}$ represents:
(1) a $C_1$-$C_6$ alkoxy group which is unsubstituted or substituted with one to three substituents selected from the group consisting of halo, amino, cyano, hydroxy, mercapto, —COOH, —CF$_3$, —OCF$_3$, —SCF$_3$, —CONH$_2$, a $C_1$-$C_6$ alkyl group, a $C_1$-$C_6$ alkoxy group, an aryl group, and a $C_3$-$C_{12}$ heterocyclic group containing one to three heteroatoms selected from O, S and N;
(2) a nitrogen-containing heterocyclic group unsubstituted or substituted with one to three substituent groups selected from a $C_1$-$C_6$ alkyl group, a $C_1$-$C_6$ alkanoyl group, and a $C_1$-$C_{20}$ alkanoyl group interrupted by one or two amino groups of formula —NR'— where R' is hydrogen or ($C_1$-$C_6$)alkyl, each of the substituent groups being unsubstituted or substituted with one to three groups selected from halo, amino, cyano, hydroxy, mercapto, —COOH, —CONH$_2$, a C$_1$-C$_6$ alkyl group, a C$_1$-C$_6$ alkoxy group, a (C$_1$-C$_6$)alkylamino group, a (C$_1$-C$_6$)dialkylamino group, an aryl group, and a C$_3$-C$_{12}$ heterocyclic group containing one to three heteroatoms selected from O, S and N; or (3) a group of formula —NHR, in which R represents: a C$_1$-C$_6$ alkyl group, a C$_1$-C$_{20}$ alkyl group interrupted by one or two amino groups of formula —NR'— where R' is hydrogen or (C$_1$-C$_6$)alkyl, an aryl group, or a C$_3$-C$_{12}$ heterocyclic group containing one to three heteroatoms selected from O, S and N, and wherein R is unsubstituted or substituted with one to three substituents selected from halo, amino, cyano, hydroxy, mercapto, —COOH, —CONH$_2$, a C$_1$-C$_6$ alkyl group, a C$_1$-C$_6$ alkoxy group, a C$_1$-C$_6$ alkanoyl group, a (C$_1$-C$_6$)alkylamino group, a (C$_1$-C$_6$)dialkylamino group, an aryl group, and a C$_3$-C$_{12}$ heterocyclic group containing one to three heteroatoms selected from O, S and N.

The preparation process of the compound of formula (II) according to this invention may be carried out in the presence of an appropriate solvent that favors the production of the compound of formula (II) from the selected chemical treatment, such as ethoxyethanol (Synthesis Ex. 6), triethylamine (Et$_3$N) and acetone (Synthesis Ex. 16), ethanol (Synthesis Ex. 17), DMF (Synthesis Ex. 18) and so forth. In addition, the reaction may advantageously proceed under microwave irradiation.

According to this invention, the compound of formula (III) may be alkoxylated or aminated using an appropriate compound of formula R$^{9A}$H, so as to provide a corresponding compound of formula (II), in which R$^{9A}$ is a unsubstituted or substituted C$_1$-C$_6$ alkoxy group, a unsubstituted or substituted nitrogen-containing heterocyclic group, or a group of formula —NHR, all of these groups having the same definitions as those defined for the compound of formula (I) described above.

According to this invention, when the R$^9$ group of the compound of formula (II) has a reactive terminal group such as amino, halo and so forth, it may be further chemically modified to another group that falls within the definition of the R$^9$ group. For example, when the compound of formula (II) has a piperazin-1-yl group at the site of R$^9$, it may be reacted with a further compound of formula R$^9$H, thus giving another compound of formula (II) with a different R$^9$ group. Representative examples of the chemical modification of the R$^9$ group are provided in Table 1, infra.

In contrast to the two-step preparation process of the compound of formula (III) as disclosed in JP 09143166 A2, in this invention, the applicants developed a novel one-step process for the preparation of the compound of formula (III), which comprises reacting a compound of formula (IV) with POCl$_3$:

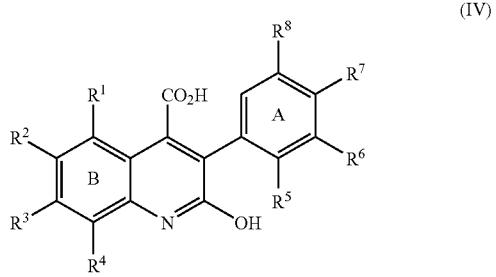

(IV)

wherein the R$^1$-R$^8$ groups have the same definitions as those defined for the compound of formula (I) described above.

The preparation process of the compound of formula (III) according to this invention is simple and can be performed without using a solvent.

The chloro atom present in the compound of formula (III) may be converted to hydrogen by reacting the compound of formula (III) with sodium metal in the presence of ethanol (see Synthesis Ex 8, infra).

The chloro atom present in the compound of formula (III) may be converted to hydroxyl by treating the compound of formula (III) with a 36% HCl aqueous solution.

The chloro atom present in the compound of formula (III) may be converted to fluoro by reacting the compound of formula (III) with tetrabutylphosphonium hydrogendifluoride in the presence of xylene, or by reacting the compound of formula (III) with KF in the presence of dimethylsulfone.

The chloro atom present in the compound of formula (III) may be converted to bromo by reacting the compound of formula (IV) with POBr$_3$, or with trimethylsilyl bromide (Me$_3$SiBr).

The chloro atom present in the compound of formula (III) may be converted to fluoro by reacting the compound of formula (III) with Me$_3$SiCl/NaI (M. Schlossor et al. (2002), Eur, J, Org, Chem., 24:4181-4184), or with NaI/HI (O. Sugimoto et al. (2001), Helv. Chim. Acta., 84:1112-1118).

The compound of formula (IV) may be prepared from the reaction of an isatin of formula (V) and a pheylacetic acid of formula (VI):

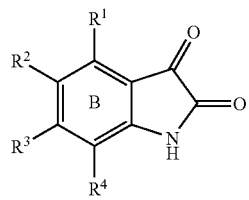

(V)

wherein the R$^1$-R$^4$ groups have the same definitions as those defined for the compound of formula (I) described above; and

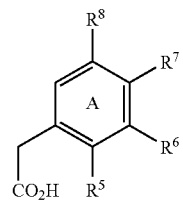

(VI)

wherein the R$^5$-R$^8$ groups have the same definitions as those defined for the compound of formula (I) described above.

Isatins (indole-2,3-diones) of formula (V) are versatile starting materials for a variety of important classes of heterocyclic compounds. Isatins of formula (V) are commercially available or may be prepared according to the processes known in the art.

Representative examples of isatins useful in this invention include, but are not limited to: isatin, 4-bromoisatin, 5-bromoisatin, 5-fluoroisatin, 5-chloroisatin, 5-methylisatin, 5-nitroisatin, 5-iodoisatin, 5-butylisatin, 5-methoxyisatin, 5-(trifluoromethoxy)isatin, 5-methylthioisatin, 5-(3'-methylbuten-2'-yl)isatin, 6-(3'-methylbuten-2'-yl)isatin, 6-benzoylisatin, 7-ethylisatin, 7-fluoroisatin, 7-bromoisatin, 7-(trifluoromethyl)isatin, 4-methyl-5-bromoisatin, 4,5-dimethylisatin, 4,6-dichloroisatin, 4,6-difluoroisatin, 4,6-dimethylisatin, 4,6-bis(trifluoromethyl)isatin, 4,7-dichloroisatin, 4-chloro-7-methoxyisatin, 5-chloro-7-methylisatin, 5,6-diethylisatin, 5,6-dimethylisatin, 5,6-dimethoxyisatin, 5-bromo-6-methylisatin, 5-bromo-7-methyl-1H-indole-2,3-dione, 5,7-dimethylisatin, 6-chloro-7-methylisatin, 6-fluoro-5-methylisatin, 6-iodo-4-trifluoromethylisatin, 7-fluoro-4-methylisatin, 7-fluoro-5-methylisatin, 7-methyl-5-nitro-1H-indole-2,3-dione, 7-fluoro-6-methylisatin, 4-bromo-5-fluoro-7-methylisatin, 5,6-dichloro-4-nitroisatin, 5,6-dibromo4-nitroisatin, 5,6-difluoro4-nitroisatin, 6,7-dibromo-4-methoxyisatin, 5,6-dimethyl-4-nitroisatin, 4,5,6-trichloroisatin, 4,5-benzoisatin, 5,6-benzoisatin, 6,7-benzoisatin, melosatin A, methyl isatin-4-carboxylate, and 1,5,6,7-tetrahydro-1-aza-s-indacene-2,3-dione.

Concerning the preparation processes of isatins known in the art, reference may be made to, e.g., Lu Zhou et al. (2006), *J. Med. Chem.*, 49:3440-3443; Pedro J. Montoya-Pelaez et al. (2006), *J. Org. Chem.*, 16:5921-5929; Michael C. Pimung et al. (2005), *J. Med. Chem.*, 48:3045-3050; Panagiotis Polychronopoulos et al. (2004), *J. Med. Chem.*, 47:935-946; Miguel F. Brana et al. (2004), *J. Med. Chem.*, 47:2236-2242; Teruhisa Tokunaga et al. (2001), *J. Med. Chem.*, 44:4641-4649; Laurence P. G. Wakelin et al (2003), *J. Med. Chem.*, 46:5790-5802; and Timur Guengoer et al. (2006), *J. Med. Chem.* 49:2440-2455.

Besides, isatins can be easily prepared from inexpensive and available anilines (Holt, J. S. et al. (1958), *J. Chem. Soc.*, pp. 1217-1223; Huntress, E. H. et al. (1949), *J. Am. Chem. Soc.*, 71:745-746; Maginnity, P. M. et al. (1951), *J. Am. Chem. Soc.*, 73: 3579-3580, see U.S. Pat. No. 6,034,266).

Phenylacetic acids of formula (VI) are commercially available or may be prepared according to the processes known in the art.

Representative examples of phenylacetic acids of formula (VI) useful in this invention include, but are not limited to: 2-bromophenylacetic acid, 2-fluorophenylacetic acid, 2-(aminomethyl)phenylacetic acid, 2-benzyloxyphenylacetic acid, 2-(trifluoromethyl)phenylacetic acid, 2-(trifluoromethoxy)phenylacetic acid, 2-(2,6-dichloroanilino)phenylacetic acid, 3-bromophenylacetic acid, 3-fluorophenylacetic acid, 3-iodophenylacetic acid, 3-benzyloxyphenylacetic acid, 3-trifluoromethyl)phenylacetic acid, 3-(trifluoromethoxy)phenylacetic acid, 4-bromophenylacetic acid, 4-fluorophenylacetic acid, 4-hydroxyphenylacetic acid, 4-mercaptophenylacetic acid, 4-aminophenylacetic acid, 4-(bromomethyl)phenylacetic acid, 4-(hydroxymethyl)phenylacetic acid, 4-(methylthio)phenylacetic acid, 4-(trifluoromethoxy)phenylacetic acid, 4-(trifluoromethylthio)phenylacetic acid, 4-biphenylacetic acid, 4-(phenoxy)phenylacetic acid, 4-(benzyloxy)phenylacetic acid, 2-amino-4-fluorophenylacetic acid, 2-bromo-4-fluorophenylacetic acid, 2-fluoro-4-methoxyphenylacetic acid, 2-chloro-4-fluorophenylacetic acid, 2-chloro-4-hydroxyphenylacetic acid, 2-chloro-5-fluorophenylacetic acid, 2-chloro-6-fluorophenylacetic acid, 2,3-difluorophenylacetic acid, 2,4-difluorophenylacetic acid, 2,5-difluorophenylacetic acid, 2,5-dibromophenylacetic acid, 2,5-dimethylphenylacetic acid, 2,5-dimethoxyphenylacetic acid, 2,4-bis(trifluoromethyl)phenylacetic acid, 3-chloro-2-fluorophenylacetic acid, 3-chloro-4-fluorophenylacetic acid, 3-methoxy-4-hydroxyphenylacetic acid, 3-chloro-5-fluorophenylacetic acid, 3-fluoro-4-methylphenylacetic acid, 3-ethoxy-4-ethoxycarbonyl phenylacetic acid, 3,4-difluorophenylacetic acid, 3,5-difluorophenylacetic acid, 3,5-dihydroxy phenylacetic acid, 3,5-bis(trifluoromethyl) phenylacetic acid, 4-chloro-2-fluorophenylacetic acid, 4-chlor-3-nitrophenylacetic acid, 4-chloro-3-fluorophenylacetic acid, 5-chloro-2-fluorophenylacetic acid, 5-methoxy-2-nitrophenylacetic acid, 2,3,4-trifluorophenylacetic acid, 2,4,5-trifluorophenylacetic acid, 2-chloro-3,6-difluorophenylacetic acid, 2-chloro-4,5-difluorophenylacetic acid, 2-chloro-6-fluoro-3-methylphenylacetic acid, 3-chloro-2,4-difluorophenylacetic acid, 3-chloro-2,6-difluorophenylacetic acid, 3,5-dimethoxy-4-hydroxyphenylacelic acid, 4-chloro-2,6-difluorophenylacetic acid, 6-chloro-2-fluoro-3-methylphenylacetic acid, and 3,5-dichloro-4-[(4-hydroxy-3-isopropylphenoxy)]phenylacetic acid.

Concerning the preparation processes of phenylacetic acids known in the art, reference may be made to, e.g., Bruce G. Szczepankiewicz, et al. (2006), *J. Med. Chem.*, 49:3563-3580; and You-Chu Wang et al. (2002), *Org. Lett.*, 4:2675-2678.

The compounds of formula (I) according to this invention, as well as their synthesis precursors of formula (II), have been proved to possess excellent activities against the growth of cancer cells, in particular human cervical epithelioid carcinoma (HeLa), hepatocellular carcinoma (SKHep1), oral squamous cell carcinoma (SAS), human stomach adenocarcinoma (AGS), human renal clear cell carcinoma (RCC 768-O), and esophageal carcinoma (CE81T). It is thus contemplated that the compounds of formula (I) according to this invention can be used in the treatment of tumors or cancers in a subject, including human and other mammals.

Therefore, this invention provides a method of treating a subject having a cancer disease comprising administering to the subject a compound of formula (I) or a pharmaceutically acceptable salt or solvate thereof as described above.

The compounds of formula (I) according to this invention may be in their free form or in the form of a pharmaceutically acceptable salt thereof. In addition, the compounds of formula (I) according to this invention may also exist as a stereoisomer or in the form of solvates represented by the hydrate. Therefore, it is contemplated that these stereoisomers and solvates fall within the technical concept of this invention.

As used herein, the pharmaceutically acceptable salt includes, but is not limited to: salts with inorganic acids, such as hydrochloride, hydrobromide, sulfate and phosphate; salts with organic acids, such as acetate, maleate, tartrate, methanesulfonate; and salts with amino acids, such as arginine, aspartic acid and glutamic acid.

This invention also envisions the application of compounds of formula (I) according to this invention, or a pharmaceutically acceptable salt or solvate thereof, in the manufacture of pharmaceutical compositions for use in tumor/cancer therapy. Therefore, this invention provides a pharmaceutical composition comprising a compound of formula (I) as described above, or a pharmaceutically acceptable salt or solvate thereof, for the treatment of tumors or cancers in a subject, including human and other mammals.

Optionally, the pharmaceutical composition according to this invention may additionally contain a pharmaceutically acceptable carrier commonly used in the art for the manufacture of medicaments For example, the pharmaceutically acceptable carrier can include one or more than one of the following reagents: solvents, disintegrating agents, binders, excipients, lubricants, absorption delaying agents and the like.

The pharmaceutical composition according to this invention may be administered parenterally or orally in a suitable pharmaceutical form. Suitable pharmaceutical forms include sterile aqueous solutions or dispersions, sterile powders, tablets, troches, pills, capsules, and the like.

EXAMPLES

The present invention will be described in more detail with reference to the following examples, which are given for the purpose of illustration only and are not intended to limit the scope of the present invention.

The compounds of formula (I) according to this invention can be prepared according to the following reaction schemes and protocols.

As shown in Scheme 1, reaction of isatin (1) and phenylacetic acid (2) gives 2-hydroxy-3-phenylquinoline-4-carboxylic acid (3), which may be treated with $POCl_3$ to yield 6-chloro-11H-indeno[1,2-c]quinolin-11-one (4). Reaction of a compound 4 with a compound of formula $R^{9A}H$, such as piperazine, yields a compound 5, such as 6-(piperazin-1-yl)-11H-indeno[1,2-c]quinolin-11-one (compd. 5x in Synthesis Ex. 9, infra), which may be reacted either with $NH_2OH$, optionally followed by alkylation with an alkyl halide of formula $R^{10}X$, or with $NH_2OR^{10}$ directly, to give a corresponding compound of formula (I).

Scheme 1

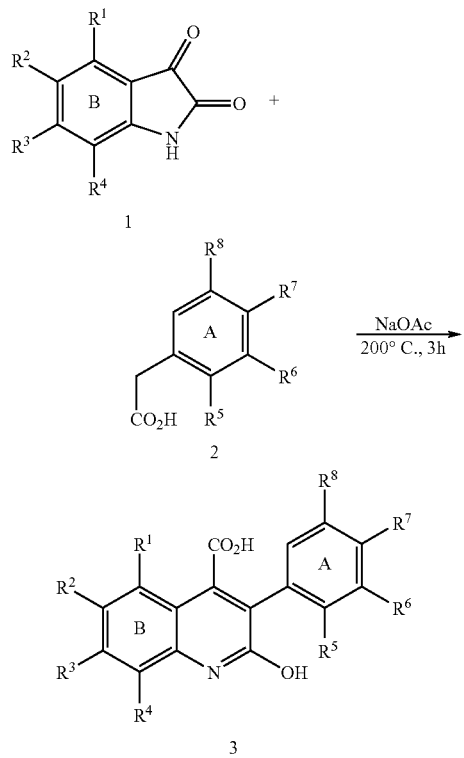

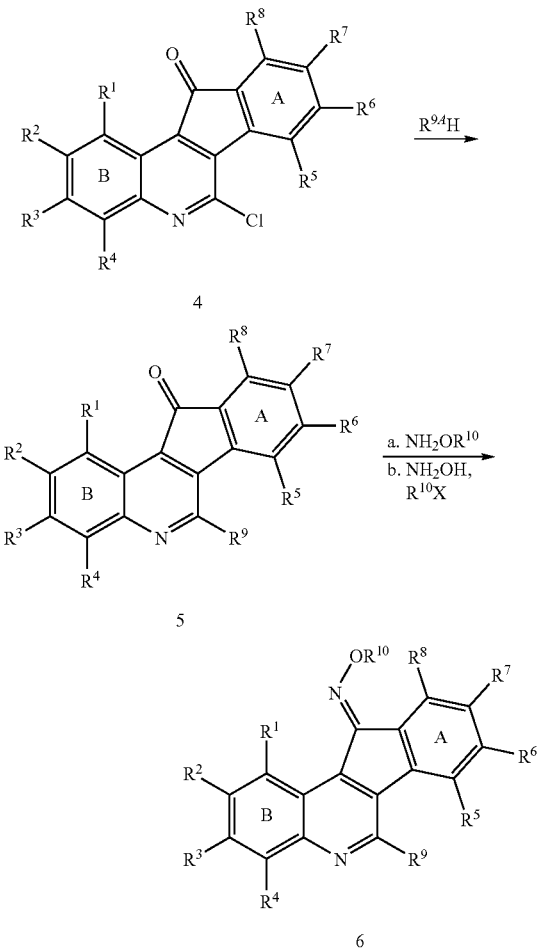

Representative compounds of formula (I) according to this invention and their synthetic precursors are shown in the following Table 1.

TABLE 1

The structures of representative compounds of formula (I) according to this invention and their synthetic precursors.

| Compd. | B ring | A ring | | $R^9$ | $R^{10}$ |
|---|---|---|---|---|---|
| 3a | $R^2$ = H | $R^7$ = H | | — | — |
| 3b | $R^2$ = H | $R^7$ = —OMe | | — | — |
| 3c | $R^2$ = H | $R^6$ = —OMe | | — | — |
| 3d | $R^2$ = H | $R^6$ = —OMe | $R^7$ = —OMe | — | — |
| 3e | $R^2$ = F | $R^7$ = —OMe | | — | — |
| 3f | $R^2$ = Cl | $R^7$ = —OMe | | — | — |
| 3g | $R^2$ = Cl | $R^6$ = —OMe | $R^7$ = —OMe | — | — |
| 4a | $R^2$ = H | $R^7$ = H | | — | — |

TABLE 1-continued

The structures of representative compounds of formula (I) according to this invention and their synthetic precursors.

| Compd. | B ring | A ring | R⁹ | R¹⁰ |
|---|---|---|---|---|
| 4b | R² = H | R⁷ = —OMe | — | — |
| 4c | R² = H | R⁶ = —OMe | — | — |
| 4d | R² = H | R⁶ = —OMe<br>R⁷ = —OMe | — | — |
| 4e | R² = F | R⁷ = —OMe | — | — |
| 4f | R² = Cl | R⁷ = —OMe | — | — |
| 4g | R² = Cl | R⁶ = —OMe<br>R⁷ = —OMe | — | — |
| 5a | R² = H | R⁷ = H | —NH—CH₂CH₂—NMe₂ | — |
| 5b | R² = H | R⁷ = H | —NH—CH₂CH₂CH₂—NMe₂ | — |
| 5c | R² = H | R⁷ = H | —NH—CH₂CH₂—NH—CH₂CH₂—OH | — |
| 5d | R² = H | R⁷ = —OMe | H | — |
| 5e | R² = H | R⁷ = —OMe | —OH | — |
| 5f | R² = H | R⁷ = —OMe | —OMe | — |
| 5g | R² = H | R⁷ = —OMe | —OEt | — |
| 5h | R² = H | R⁷ = —OMe | —NH—CH₂CH₂—OEt | — |
| 5i | R² = H | R⁷ = —OMe | —NH—CH₂CH₂CH₂—NMe₂ | — |
| 5j | R² = H | R⁷ = —OMe | —NH—(4-F-C₆H₄) | — |
| 5k | R² = H | R⁷ = —OMe | —NH—(4-Cl-C₆H₄) | — |
| 5l | R² = H | R⁷ = —OMe | —NH—(2,4-F₂-C₆H₃) | — |

TABLE 1-continued

The structures of representative compounds of formula (I) according to this invention and their synthetic precursors.

| Compd. | B ring | A ring | R⁹ | R¹⁰ |
|---|---|---|---|---|
| 5m | R² = H | R⁷ = —OMe | —NH—(3,4-difluorophenyl) | — |
| 5n | R² = H | R⁷ = —OMe | —NH—(2,4-dichlorophenyl) | — |
| 5o | R² = H | R⁷ = —OMe | —NH—(4-methoxyphenyl) | — |
| 5p | R² = H | R⁷ = —OMe | —NH—(3-methoxyphenyl) | — |
| 5q | R² = H | R⁷ = —OMe | —NH—(2,4-dimethoxyphenyl) | — |
| 5r | R² = H | R⁷ = —OMe | —NH—(3,4-dimethoxyphenyl) | — |
| 5s | R² = H | R⁷ = —OMe | —NH—(4-acetylphenyl) | — |
| 5t | R² = H | R⁷ = —OMe | —NH—(3-acetylphenyl) | — |
| 5u | R² = H | R⁷ = —OMe | —NH—(2-methoxycarbonylphenyl) | — |
| 5v | R² = H | R⁷ = —OMe | 3-aminopyrrolidin-1-yl | — |

TABLE 1-continued

The structures of representative compounds of formula (I) according to this invention and their synthetic precursors.

| Compd. | B ring | A ring | R⁹ | R¹⁰ |
|---|---|---|---|---|
| 5w | R² = H | R⁷ = —OMe | 4-aminopiperidin-1-yl | — |
| 5x | R² = H | R⁷ = —OMe | piperazin-1-yl | — |
| 5y | R² = H | R⁷ = —OMe | 3-methylpiperazin-1-yl | — |
| 5z | R² = H | R⁷ = —OMe | 1,4-diazepan-1-yl | — |
| 5aa | R² = H | R⁷ = H | piperazin-1-yl | — |
| 5bb | R² = H | R⁸ = —OMe | piperazin-1-yl | — |
| 5cc | R² = H | R⁸ = —OMe | piperazin-1-yl | — |
| 5dd | R² = H | R⁶ = —OMe<br>R⁷ = —OMe | piperazin-1-yl | — |
| 5ee | R² = F | R⁷ = —OMe | piperazin-1-yl | — |
| 5ff | R² = Cl | R⁷ = —OMe<br>R⁸ = —OMe | piperazin-1-yl | — |
| 5gg | R² = H | R⁷ = —OMe | 4-(2-chloroacetyl)piperazin-1-yl | — |
| 5hh | R² = H | R⁷ = —OMe | 4-(3-chloropropanoyl)piperazin-1-yl | — |

TABLE 1-continued

The structures of representative compounds of formula (I) according to this invention and their synthetic precursors.

| Compd. | B ring | A ring | $R^9$ | $R^{10}$ |
|---|---|---|---|---|
| 5ii | $R^2$ = H | $R^7$ = —OMe | piperazine-C(O)-CH$_2$CH$_2$CH$_2$-Cl | — |
| 5jj | $R^2$ = H | $R^7$ = —OMe | piperazine-C(O)-CH$_2$-OH | — |
| 5kk | $R^2$ = H | $R^7$ = —OMe | piperazine-C(O)-CH$_2$-NHMe | — |
| 5ll | $R^2$ = H | $R^7$ = —OMe | piperazine-C(O)-CH$_2$-NMe$_2$ | — |
| 5mm | $R^2$ = H | $R^7$ = —OMe | piperazine-C(O)-CH$_2$-NH-CH$_2$CH$_2$-NH$_2$ | — |
| 5nn | $R^2$ = H | $R^7$ = —OMe | piperazine-C(O)-CH$_2$-NH-CH$_2$CH$_2$-OH | — |
| 5oo | $R^2$ = H | $R^7$ = —OMe | piperazine-C(O)-CH$_2$-NH-CH$_2$CH$_2$-NMe$_2$ | — |
| 5pp | $R^2$ = H | $R^7$ = —OMe | piperazine-C(O)-CH$_2$-NH-CH$_2$CH$_2$CH$_2$-NMe$_2$ | — |
| 5qq | $R^2$ = H | $R^7$ = —OMe | piperazine-C(O)-CH$_2$-NH-CH$_2$CH$_2$-NH-CH$_2$CH$_2$-NH$_2$ | — |
| 5rr | $R^2$ = H | $R^7$ = —OMe | piperazine-C(O)-CH$_2$-NH-CH$_2$CH$_2$-NH-CH$_2$CH$_2$-OH | — |
| 5ss | $R^2$ = H | $R^7$ = —OMe | piperazine-C(O)-CH$_2$-NH-CH$_2$CH$_2$CH$_2$-N(Me)-CH$_2$CH$_2$CH$_2$-NH$_2$ | — |

TABLE 1-continued

The structures of representative compounds of formula (I) according to this invention and their synthetic precursors.

| Compd. | B ring | A ring | R⁹ | R¹⁰ |
|---|---|---|---|---|
| 5tt | R² = H | R⁷ = —OMe | piperazine-N-C(O)-CH₂-piperazine-NH | — |
| 5uu | R² = H | R⁷ = —OMe | piperazine-N-C(O)-CH₂-morpholine | — |
| 5vv | R² = H | R⁷ = —OMe | piperazine-N-C(O)-CH₂-NH-CH₂CH₂-piperazine-NH | — |
| 5ww | R² = H | R⁷ = —OMe | piperazine-N-C(O)-CH₂CH₂-OH | — |
| 5xx | R² = H | R⁷ = —OMe | piperazine-N-C(O)-CH₂CH₂-NHMe | — |
| 5yy | R² = H | R⁷ = —OMe | piperazine-N-C(O)-CH₂CH₂-NMe₂ | — |
| 5zz | R² = H | R⁷ = —OMe | piperazine-N-C(O)-CH₂CH₂-NH-CH₂CH₂-NH₂ | — |
| 5aaa | R² = H | R⁷ = —OMe | piperazine-N-C(O)-CH₂CH₂-NH-CH₂CH₂-OH | — |
| 5bbb | R² = H | R⁷ = —OMe | piperazine-N-C(O)-CH₂CH₂-NH-CH₂CH₂-NMe₂ | — |
| 5ccc | R² = H | R⁷ = —OMe | piperazine-N-C(O)-CH₂CH₂-NH-CH₂CH₂CH₂-NMe₂ | — |

TABLE 1-continued

The structures of representative compounds of formula (I) according to this invention and their synthetic precursors.

| Compd. | B ring | A ring | R⁹ | R¹⁰ |
|---|---|---|---|---|
| 5ddd | R² = H | R⁷ = —OMe | piperazine-C(O)-CH₂CH₂-NH-CH₂CH₂-NH-CH₂CH₂-NH₂ | — |
| 5eee | R² = H | R⁷ = —OMe | piperazine-C(O)-CH₂CH₂-NH-CH₂CH₂-NH-CH₂CH₂-OH | — |
| 5fff | R² = H | R⁷ = —OMe | piperazine-C(O)-CH₂CH₂-NH-CH₂CH₂CH₂-N(Me)-CH₂CH₂CH₂-NH₂ | — |
| 5ggg | R² = H | R⁷ = —OMe | piperazine-C(O)-CH₂CH₂-piperazine-NH | — |
| 5hhh | R² = H | R⁷ = —OMe | piperazine-C(O)-CH₂CH₂-morpholine | — |
| 5iii | R² = H | R⁷ = —OMe | piperazine-C(O)-CH₂CH₂-NH-CH₂CH₂-piperazine-NH | — |
| 5jjj | R² = H | R⁷ = —OMe | piperazine-C(O)-CH₂CH₂CH₂-NMe₂ | — |
| 5kkk | R² = H | R⁷ = —OMe | piperazine-CH₂-epoxide | — |
| 5lll | R² = H | R⁷ = —OMe | piperazine-CH₂-CH(OH)-CH₂-NHMe | — |
| 5mmm | R² = H | R⁷ = —OMe | piperazine-CH₂-CH(OH)-CH₂-NMe₂ | — |
| 6a | R² = H | R⁷ = —OMe | H | H |
| 6b | R² = H | R⁷ = —OMe | H | Me |
| 6c | R² = H | R⁷ = —OMe | —OH | H |
| 6d | R² = H | R⁷ = —OMe | —OMe | Me |
| 6e | R² = H | R⁷ = —OMe | —OMe | H |

TABLE 1-continued

The structures of representative compounds of formula (I) according to this invention and their synthetic precursors.

| Compd. | B ring | A ring | R⁹ | R¹⁰ |
|---|---|---|---|---|
| 6f | R² = H | R⁷ = —OMe | —NHOMe | Me |
| 6g | R² = H | R⁷ = —OMe | 2-acetylanilino (—NH—C₆H₄—C(O)Me) | H |
| 6h | R² = H | R⁷ = —OMe | 2-acetylanilino (—NH—C₆H₄—C(O)Me) | Me |
| 6i | R² = H | R⁷ = —H | piperazin-1-yl | H |
| 6j | R² = H | R⁷ = —H | piperazin-1-yl | Me |
| 6k | R² = H | R⁷ = —F | piperazin-1-yl | H |
| 6l | R² = H | R⁷ = —F | piperazin-1-yl | Me |
| 6m | R² = H | R⁷ = —OMe | 4-(3-(dimethylamino)propanoyl)piperazin-1-yl | Me |
| 6n | R² = H | R⁷ = —OMe | 4-(3-((2-(dimethylamino)ethyl)amino)propanoyl)piperazin-1-yl | H |
| 6o | R² = H | R⁷ = —OMe | 4-(3-((2-(dimethylamino)ethyl)amino)propanoyl)piperazin-1-yl | Me |
| 6p | R² = H | R⁷ = —OMe | piperazin-1-yl | H |
| 6q | R² = H | R⁷ = —OMe | piperazin-1-yl | Me |

TABLE 1-continued

The structures of representative compounds of formula (I) according to this invention and their synthetic precursors.

| Compd. | B ring | A ring | R⁹ | R¹⁰ |
|---|---|---|---|---|
| 6r | $R^2$ = H | $R^7$ = —OMe | piperazinyl (N–...–NH) | —CH₂CH₂—NMe₂ |
| 6s | $R^2$ = H | $R^7$ = —OMe | piperazinyl (N–...–NH) | —CH₂CH₂CH₂—NMe₂ |
| 6t | $R^2$ = H | $R^7$ = —OMe | piperazinyl (N–...–NH) | —CH₂CH₂CH₂—NH₂ |
| 6u | $R^2$ = H | $R^7$ = —OMe | piperazinyl (N–...–NH) | —CH₂CH₂—N(pyrrolidinyl) |
| 6v | $R^2$ = H | $R^7$ = —OMe | piperazinyl (N–...–NH) | —CH₂CH₂—N(piperidinyl) |
| 6w | $R^2$ = H | $R^7$ = —OMe | piperazinyl (N–...–NH) | —CH₂CH₂—N(morpholinyl) |
| 6x | $R^2$ = H | $R^7$ = —OMe | piperazinyl (N–...–NH) | —CH₂—phenyl |
| 6y | $R^2$ = H | $R^7$ = —OMe | piperazinyl-N-CH₂-(oxiranyl) | —CH₂-(oxiranyl) |
| 6z | $R^2$ = H | $R^7$ = —OMe | piperazinyl-N-CH₂CH(OH)CH₂NMe₂ | —CH₂CH(OH)CH₂NMe₂ |
| 6aa | $R^2$ = H | $R^7$ = —OMe | H | —CH₂CH₂—N(pyrrolidinyl) |
| 6bb | $R^2$ = H | $R^7$ = —OMe | OH | —CH₂CH₂—N(pyrrolidinyl) |

Note:
—OMe represents methoxy; —OEt represents ethoxy; and Me represents methyl.

General Procedures:

The general TLC was performed using pre-coated (0.2 mm) silica gel 60 F₂₅₄ plates (EM Laboratories, Inc.), and detected using a UV light at 254 nm.

The melting point of each of the compounds synthesized in the following examples was detected by an uncorrected Electrothermal IA9100 digital melting-point apparatus. 5 The column chromatography was performed using silica gel 60 (sieve mesh 230-400 mm, manufactured by E. Merck Company) as the solid phase in combination with a suitable eluent for separation and purification.

$^1$H-NMR spectra were detected using a Varian Unity-400 (400 MHz) or Varian Gemini-200 (200 MHz) nuclear magnetic resonance spectrometer, with chemical shifts being represented by δ in ppm using TMS (0 ppm) as an internal standard, and coupling constants being represented by J in Hz.

Elemental analyses were carried out on a Heraeus CHN-O-Rapid elemental analyzer, and results were within ±0.4% of calc. values.

The electrospray ionization mass spectra (ESIMS) and high-resolution electronimpact mass spectra (HREIMS) were collected using a Bruker APEX I mass spectrometer.

Synthesis Ex. 1

6-Chloro-11H-indeno[1,2-c]quinolin-11-one (4a)

2.65 g (10 mmol) of 2-hydroxy-3-phenylquinoline-4-carboxylic acid (3a) was added into $POCl_3$ (30 mL) and heated at 150° C. for 48 hrs (TLC monitoring). After cooling, the mixture was poured into ice-water (150 mL) to result in precipitation, followed by filtration. The resultant filter cake was poured into 5% $NaHCO_{3(aq)}$ (200 mL) with vigorous stirring for 1 hr, washed with $H_2O$, and dried to give a brown solid, which was recrystallized with EtOH to give the title compound 4a as a red solid (2.31 g, 87% yield).

Detected Properties of the Title Compound:

M.p.:149-150° C. $^1$H—NMR(400 MHz,CDCl$_3$):3.89(s, 3H),7.35(m,1H,9-H), 7.54(m,1H,8-H),7.61(m,1H,2-H), 7.67-7.72(m,2H,3,7-H),7.96(d,1H,J=8.8 Hz,4-H),8.14(d, 1H,J=7.6 Hz,10-H),8.79(dd,1H,J=0.4,8.4 Hz, 1-H). $^{13}$C—NMR(100 MHz,CDCl$_3$):122.63, 123.98, 124.26, 124.94, 128.60, 129.69, 129.95, 131.11, 133.08, 135.36, 136.30, 136.55, 141.52, 145.03, 149.83, 193.65. Anal. calcd for C$_{16}$H$_8$ClNO·0.1 H$_2$O:C 71.35, H 3.03, N 5.20; found: C 71.64, H 3.18, N 5.23.

Synthesis Ex. 2

6-Chloro-9-methoxy-11H-indeno[1,2-c]quinolin-11-one (4b)

6-Chloro-9-methoxy-11H-indeno[1,2-c]quinolin-11-one (4b) was prepared substantially according to the procedures as set forth in the above Synthesis Example 1, except that 2-hydroxy-3-[(4-methoxy)phenyl]quinoline-4-carboxylic acid (3b) was used in place of compound 3a. Compound 4b was recrystallized from EtOH as a red solid in a yield of 91%.

Detected Properties of the Title Compound:

M.p.:227-228° C. $^1$H—NMR(400 MHz,CDCl$_3$):3.89(s, 3H,9-OMe),6.99 (dd, 1H,J=2.4,8.4 Hz,8-H),7.24(d,1H,J=2.4 Hz,10-H),7.61(m,1H,2-H), 7.67(m,1H,3-H),7.95(dd,1H, J=0.4,8.8 Hz,4-H),8.02(d,1H,J=8.4 Hz, 7-H),8.76(dd,1H, J=0.8,8.4 Hz,1-H). $^{13}$C—NMR(100 MHz,CDCl$_3$):55.81, 111.21, 119.48, 122.80, 123.97, 125.12, 128.59, 129.64, 130.61, 133.55, 135.14, 136.27, 137.20, 144.68, 149.30, 161.45, 193.63. Anal. calcd for C$_{17}$H$_{10}$ClNO$_2$:C 69.05, H 3.41, N 4.74; found: C 68.66, H 3.57, N 4.64.

Synthesis Ex. 3

6-Chloro-8,9-dimethoxy-11H-indeno[1,2-c]quinolin-11-one (4d)

A mixture of isatin (2.21 g, 15 mmol), 3,4-dimethoxyphenylacetic acid (4.91 g, 25 mmol) and sodium acetate (0.3 g) was heated at 200° C. for 3 hrs (TLC monitoring). After cooling, the mixture was added with AcOH (100 mL), and the precipitate was collected, washed with H$_2$O, and dried to give 2-hydroxy-3-[(3,4-dimethoxy)phenyl]quinoline-4-carboxylic acid as a crude intermediate, which was used in the next step without further purification.

A mixture of the crude intermediate as obtained above and POCl$_3$ (30 mL) was heated at 150° C. for 45 hrs (TLC monitoring). After cooling, the mixture was poured into ice-water (150 mL) to result in precipitation, followed by filtration. The resultant filter cake was poured into 5% NaHCO$_{3(aq)}$ (200 mL) with vigorous stirring for 1 hr, washed with H$_2$O, and dried to give a brown solid, which was recrystallized with EtOH to give the title compound 4d as a red solid (3.64 g, 79% yield).

Detected Properties of the Title Compound:

M.p.:132-133° C. $^1$H—NMR(400 MHz,CDCl$_3$):3.94,4.03 (two s,6H,8, 9-OMe),7.17(s,1H,7-H),7.58(m,1H,2-H),7.62 (s,1H,10-H),7.66 (m,1H, 3-H),7.91(d,1H,J=8.8 Hz,4-H), 8.72(dd,1H,J=0.8, 8.4 Hz,1-H).
$^{13}$C—NMR(100 MHz,CDCl$_3$):56.28, 56.41, 107.31, 107.95, 122.82, 124.07, 125.92, 128.55, 129.46, 130.80, 135.70, 136.71, 137.29, 143.87, 149.86, 150.04, 154.47, 192.66. Anal. calcd for C$_{18}$H$_{12}$ClNO$_3$:C 66.37, H 3.71, N 4.30; found: C 66.24, H 3.71, N 4.27.

Synthesis Ex. 4

2-Fluoro-6-chloro-9-methoxy-11H-indeno[1,2-c]quinolin-11-one (4e)

2-Fluoro-6-Chloro-9-methoxy-11H-indeno[1,2-c]quinolin-11-one (4e) was prepared substantially according to the procedures as set forth in the above Synthesis Example 3, except that 2-fluoroisatin and 4-methoxyphenylacetic acid were used in place of isatin and 3,4-dimethoxyphenylacetic acid. Compound 4e was recrystallized from EtOH as a red solid in a yield of 86%.

Detected Properties of the Title Compound:

M.p.:149-150° C. $^1$H—NMR(400 MHz,CDCl$_3$):3.94(s, 3H,9-OMe),7.10(dd, 1H,J=2.4,8.4 Hz,8-H),7.32(d,1H,J=2.4 Hz,10-H),7.64(ddd,1H,J=2.8,7.6,9.6 Hz,3-H),7.99(d,1H, J=8.4 Hz,7-H),8.12(dd, 1H,J=4.8,9.6 Hz,4-H),8.49(dd,1H, J=2.8,8.4 Hz,1-H). $^{13}$C—NMR(100 MHz,CDCl$_3$): 56.10, 108.29(J=25.0 Hz),112.32, 120.97, 124.33(J=12.2 Hz), 124.60 (J=27.2 Hz), 125.92, 126.58, 131.56, 134.66, 138.61, 142.74, 162.19, 162.60, 163.68 (J=214.5 Hz), 191.97. Anal. calcd for C$_{17}$H$_9$ClFNO$_2$·0.3 H$_2$O:C 63.99, H 3.03, N 4.39; found: C 63.75, H 3.05, N 4.42.

Synthesis Ex. 5

2,6-Dichloro-9,10-dimethoxy-11H-indeno[1,2-c]quinolin-11-one (4g)

2,6-Dichloro-9,10-dimethoxy-11H-indeno[1,2-c]quinolin-11-one (4g) was prepared substantially according to the procedures as set forth in the above Synthesis Example 3, except that 2-chloroisatin was used in place of isatin. Compound 4g was recrystallized from EtOH as a red solid at a yield of 49%.

Detected Properties of the Title Compound:

M.p.:149-151° C. $^1$H—NMR(400 MHz,CDCl$_3$):3.93,4.14 (two s,6H,9-, 10-OMe),6.92(s,1H,J=8.4 Hz,7-H),7.59(dd, 1H,J=2.0,8.8 Hz,3-H), 7.81(d,1H,J=8.4 Hz,8-H),8.87(d,1H, J=8.8 Hz,4-H),8.82(d,1H, J=2.0 Hz,1-H). $^{13}$C—NMR(100 MHz,CDCl$_3$):56.44, 62.25, 116.31, 119.96, 122.94, 123.32, 123.82, 129.92, 131.57, 132.75, 135.64, 136.06, 136.77, 144.90, 147.21, 150.25, 155.20, 190.47.

Synthesis Ex. 6

6-(2-(Dimethylamino)ethylamino)-11H-indeno[1,2-c]quinolin-11-one(5a)

A mixture of compound 4a (0.27 g, 1 mmol) as obtained from the above Synthesis Example 1, N,N-dimethylaminoethylamine (5 mL) and 2-ethoxyethanol (20 mL) was refluxed at 200° C. for 48 hrs. After removal of solvent in vacuo, the residue was poured into H$_2$O (50 mL) to result in precipitation, followed by filtration. The precipitate thus collected was washed with H$_2$O and then dried to give a crude solid, which was purified by column chromatography (MeOH/CH$_2$Cl$_2$=1:10) to give the title compound 5a as a red solid (0.10 g, 32% yield).

Detected Properties of the Title Compound:

M.p.:148-149° C. $^1$H—NMR(400 MHz,CDCl$_3$):2.36(s, 6H,NMe$_2$),2.68(t,2H, J=6.0 Hz,NCH$_2$),3.71 (q,2H,J=5.2 Hz,NCH$_2$),5.91(br s,1H,NH),7.25 (m,2H,Ar—H),7.26-7.52 (m,3H,Ar—H),7.61(d,1H,J=7.8 Hz,7-H),7.67(d, 1H,J=8.4 Hz,4H),8.62(dd,1H,J=0.8,8.4 Hz,1-H). $^{13}$C—NMR(100 MHz, CDCl$_3$):36.64, 45.14(2C),57.59, 118.72, 121.21, 124.07, 124.32, 124.49, 126.40, 128.03, 128.46, 129.89, 133.25, 134.43, 134.61, 142.56, 149.95, 152.73, 195.58.

Synthesis Ex. 7

6-[2-(2-Hydroxyethylamino)ethylamino]-11H-indeno[1,2-c]quinolin-11-one (5c)

6-[2-(2-Hydroxyethylamino)ethylamino]-11H-indeno[1,2-c]quinolin-11-one (5c) was prepared substantially according to the procedures as set forth in the above Synthesis Example 6, except that 2-(2-aminoethylamino)ethanol was used in place of N,N-dimethylaminoethylamine. Compound 5c was purified by column chromatography (MeOH/CH$_2$Cl$_2$=1:5), followed by dropping of concentrated HCl and recrystallization from EtOH, giving a yield of 43%.

Detected Properties of the Title Compound:

M.p.:247-249° C. $^1$H—NMR(400 MHz,DMSO-d$_6$):3.12 (t, 2H,J=5.2 Hz, NCH$_2$),3.35(t,2H,J=5.2 Hz,NCH$_2$),3.71(t, 2H,J=5.2 Hz,NCH$_2$),4.06(m, 2H,NCH$_2$),7.37(br s,1H,OH), 7.46(m,2H,Ar—H),7.65-7.70(m,3H,Ar—H), 7.88(br s,1H, NH),8.07(d,1H,J=8.4 Hz,7-H),8.21(d,1H,J=7.6 Hz, 4-H), 8.60(dd,1H,J=1.2,8.4 Hz,1-H),9.02(br s,1H,NH). $^{13}$C—NMR(100 MHz, CDCl$_3$):55.31, 114.12(2C), 119.50, 120.75, 123.96, 123.99, 128.80, 129.10, 129.32, 131.26, 131.49 (2C), 146.81, 150.73, 160.42, 167.44. Anal. calcd for C$_{20}$H$_{19}$N$_3$O$_2$·1.9 H$_2$O·2.0 HCl:C 54.51, H 5.68, N 9.54, found: C 54.31, H 5.81, N 9.41.

Synthesis Ex. 8

9-Methoxy-11H-indeno[1,2-c]quinolin-11-one (5d)

A mixture of compound 4b (0.30 g, 1 mmol) as obtained from the above Synthesis Example 2, sodium metal (0.10 g) and dry ethanol (50 mL) was refluxed for 24 hrs (by TLC monitoring). After removal of solvent in vacuo, the residue was poured into H$_2$O (50 mL) to result in precipitation, followed by filtration. The resultant precipitate was collected by filtration and dried to give a crude solid, which was purified by column chromatography (MeOH/CH$_2$Cl$_2$=1:50) to give the title compound 5d as a red solid (0.15 g, 58% yield).

Detected Properties of the Title Compound:

M.p.:195-196° C. $^1$H—NMR(400 MHz,CDCl$_3$):3.87(s, 3H,9-OMe),6.94(dd, 1H,J=2.4,8.0 Hz,8-H),7.20(d,1H,J=2.4 Hz,10-H),7.46(d,1H,J=8.4Hz,7-H),7.57-7.66(m,2H,2,3-H), 8.02(m,1H,4-H),8.72(m,1H,1-H),9.11(s,1H,6-H). $^{13}$C—NMR(100 MHz,CDCl$_3$):55.83, 111.14, 119.56, 121.77, 123.44, 123.91, 129.47, 129.65, 129.82, 133.03, 134.83, 135.37, 138.23, 143.11, 149.73, 161.44, 194.99. Anal. calcd for C$_{17}$H$_{11}$NO$_2$:C 78.15, H 4.24, N 5.36; found: C 77.95, H 4.25, N 5.35.

Synthesis Ex. 9

6-Hydroxy-9-methoxy-11H-indeno[1,2-c]quinolin-11-one (5e)

A mixture of compound 4b (0.30 g, 1 mmol) as obtained from the above Synthesis Example 2, 36% HCl (2 mL) and DMF (30 mL) was refluxed for 2 hrs (by TLC monitoring). After removal of solvent in vacuo, the residue was poured into H$_2$O (50 mL) to result in precipitation, followed by filtration. The precipitate thus collected was washed with H$_2$O and then dried to give a crude solid, which was purified by recrystallization from MeOH to give the title compound 5e as a red solid (0.09 g, 32% yield).

Detected Properties of the Title Compound:

M.p.:316-317° C. $^1$H—NMR(400 MHz,DMSO-d$_6$):3.83 (s,3H,9-OMe),7.04 (dd,1H,J=2.4,8.0 Hz,8-H),7.14(d,1H, J=2.0 Hz,10-H),7.26(m,1H, 3-H),7.37(d,1H,J=8.4 Hz,4-H), 7.51(m,1H,2-H),7.81(d,1H,J=8.0 Hz, 7-H),8.34(d,1H,J=8.4 Hz,1-H),12.32(br s,1H,OH). $^{13}$C—NMR(100 MHz, CDCl$_3$): 55.72, 111.14, 114.79, 115.64, 118.17, 123.10, 124.37, 130.16, 133.13, 133.37, 133.90, 134.67, 137.78, 139.76, 158.71, 160.55, 195.10.

HRMS (ESI) calc. for C$_{17}$H$_{12}$NO$_3$(M+):278.0817; found: 278.0818.

Synthesis Ex. 10

6-[3-(Dimethylamino)propylamino]-9-methoxy-11H-indeno[1,2-c]quinolin-11-one (5i)

6-[3-(Dimethylamino)propylamino]-9-methoxy-11H-indeno [1,2-c]quinolin-11-one (5i) was prepared substantially according to the procedures as set forth in the above Synthesis Example 6, except that compound 4b as obtained from the above Synthesis Example 2 and N,N-dimethylaminopropylamine were used in place of compound 4a and N,N-dimethylaminoethylamine, respectively. Compound 5i was recrystallized from EtOH at a yield of 61%.

Detected Properties of the Title Compound;

M.p.:113-114° C. $^1$H—NMR(400 MHz,CDCl$_3$):1.89(m, 2H,NCH$_2$CH$_2$CH$_2$N), 2.33(s,6H,NMe$_2$),2.58(m,2H,NCH$_2$), 3.79(m,2H,NCH$_2$),3.85(s,3H, 9-OMe),6.82(dd,1H,J=2.8,8.4 Hz,8-H),7.16(br s,1H,NH),7.19(d,1H,J=2.8 Hz,10-H),7.25 (m,1H,2-H),7.46(m,2H,3-H,7-H),7.66(d,1H,J=8.4 Hz,4-H), 8.58(dd,1H,J=1.6,8.0 Hz,1-H). $^{13}$C—NMR(100 MHz, CDCl$_3$): 24.99, 42.98, 45.75 (2C), 55.69, 60.04, 111.09, 117.94, 118.69, 122.04, 123.71, 123.97, 126.26, 129.07, 129.26, 133.92, 134.67, 135.31, 149.39, 152.32, 160.24, 195.68. HREIMS for C$_{22}$H$_{23}$N$_3$O$_2$:361.1790; found: 361.1788.

Synthesis Ex. 11

6-(4-Acetylphenylamino)-9-methoxy-11H-indeno[1,2-c]quinolin-11-one (5s)

A mixture of compound 4b (0.30 g, 1 mmol) as obtained from the above Synthesis Example 2, 4-aminoacetophenone (0.42 g, 3 mmol) and 2-ethoxyethanol (20 mL) was heated with stirring under microwave irradiation (150 W) for 30 min (by TLC monitoring). After removal of solvent in vacuo, the residue was poured into $H_2O$ (50 mL) to result in precipitation, followed by filtration. The precipitate thus collected was washed with $H_2O$ and then dried to give a crude solid, which was purified by recrystallization from MeOH to give the title compound 5s as a red solid (0.33 g, 84% yield).

Detected Properties of the Title Compound:
M.p.:251-252° C. $^1$H—NMR(400 MHz,DMSO-$d_6$):2.54 (s,3H,Me),3.84(s, 3H,9-OMe),7.08(dd,1H,J=2.8,8.4 Hz,8-H),7.18(d,1H,J=2.8 Hz,10-H), 7.47(m,1H,2-H),7.60(m,1H, 3-H),7.70(d,1H,J=8.0 Hz,4-H),7.74(d, 1H,J=8.4 Hz,1-H), 7.79(m,2H,Ar—H),7.94(m,2H,Ar—H),8.53(dd,1H,J=0.8, 8.0 Hz,7-H). $^{13}$C—NMR(100 MHz,DMSO-$d_6$):26.33, 55.82, 110.97, 118.25 (2C), 118.72, 120.05, 122.96, 125.23, 126.72, 127.16, 129.37 (2C), 129.90, 130.06, 131.04, 133.04, 134.56, 134.69, 145.90, 147.69, 148.56, 160.52, 194.38, 196.16. Anal. calcd for $C_{25}H_{18}N_2O_3 \cdot 0.7\ H_2O$:C 73.76, H 4.81, N 6.88; found: C 73.49, H 4.86, N

Synthesis Ex. 12

9-Methoxy-6-(piperazin-1-yl)-11H-indeno[1,2-c]quinolin-11-one (5x)

A mixture of compound 4b (0.30 g, 1 mmol) as obtained from the above Synthesis Example 2, piperazine (0.45 g, 5 mmol) and 2-ethoxyethanol (20 mL) was heated with stirring under microwave irradiation (150 W) for 30 min (by TLC monitoring). After removal of solvent in vacuo, the residue was poured into $H_2O$ (50 mL) to result in precipitation, followed by filtration. The precipitate thus collected was washed with $H_2O$ and then dried to give a crude solid, which was purified by recrystallization from MeOH to give the title compound 5x as a red solid (0.29 g, 83% yield).

Detected Properties of the Title Compound:
M.p.:150-151° C. $^1$H—NMR(400 MHz,DMSO-$d_6$):3.29 (m,4H,piperazinyl-H), 3.45(m,4H,piperazinyl-H),3.85(s,3H, 9-OMe),7.12(dd,1H,J=2.0,8.0 Hz, 8-H),7.17(d,1H,J=2.0 Hz,10-H),7.50-7.56(m,2H,2-,7-H),7.64(m,1H, 3-H),7.79(d, 1H,J=8.4 Hz,4-H),8.54(d,1H,J=8.4 Hz,1-H). $^{13}$C—NMR (100 MHz,DMSO-$d_6$):42.80 (2C), 47.10 (2C), 55.84, 111.01, 119.27, 120.41, 122.98, 124.77, 127.38, 127.79, 129.83, 132.34, 133.81, 134.43, 135.37, 147.62, 155.93, 160.55, 194.35. Anal. calcd for $C_{21}H_{19}N_3O_2 \cdot 0.7\ H_2O \cdot 0.8\ HCl$: C 65.15, H 5.52, N 10.85; found:C 65.38, H 5.45, N 10.59.

Synthesis Ex. 13

8,9-Dimethoxy-6-(piperazin-1-yl)-11H-indeno[1,2-c]quinolin-11-one (5dd)

8,9-Dimethoxy-6-(piperazin-1-yl)-11H-indeno[1,2-c]quinolin-11-one (5dd) was prepared substantially according to the procedures as set forth in the above Synthesis Example 12, except that compound 4d as obtained from the above Synthesis Example 3 was used in place of compound 4b. Compound 5dd was recrystallized from EtOH at a yield of 46%.

Detected Properties of the Title Compound:
M.p.:135-136° C. $^1$H—NMR(400 MHz,CDCl$_3$):3.17(m, 4H,piperazinyl-H), 3.35(m,4H,piperazinyl-H),3.94,4.04 (two s,6H,8-,9-OMe),7.19(s,1H, 7-H),7.32(s,1H,10-H),7.43 (m,1H,2-H),7.55(m,1H,3-H),7.82(dd,1H,J=0.8,8.0 Hz,4-H), 8.68(dd,1H,J=1.6,8.4 Hz,1-H). $^{13}$C—NMR(100 MHz, CDCl$_3$):46.14 (2C), 51.30 (2C), 56.29, 56.50, 107.26, 107.85, 121.09, 123.76, 125.74, 126.87, 127.98, 129.52, 131.34, 136.74, 138.27, 149.07, 149.15, 153.96, 157.01, 194.55. Anal. calcd for $C_{22}H_{21}N_3O_3 \cdot 0.5\ HCl$: C 67.13, H 5.51, N 10.68; found: C 67.17, H 5.84, N 10.77.

Synthesis Ex. 14

2-Fluoro-9-methoxy-6-(piperazin-1-yl)-11H-indeno[1,2-c]quinolin-11-one (5ee)

2-Fluoro-9-methoxy-6-(piperazin-1-yl)-11H-indeno[1,2-c]quinolin-11-one (5ee) was prepared substantially according to the procedures as set forth in the above Synthesis Example 12, except that compound 4e as obtained from the above Synthesis Example 4 was used in place of compound 4b. Compound 5ee was recrystallized from EtOH at a yield of 57%.

Detected Properties of the Title Compound:
M.p.:157-158° C. $^1$H—NMR(400 MHz,DMSO-$d_6$):2.97 (m,4H,piperazinyl-H), 3.16(m,4H,piperazinyl-H),3.84(s,3H, 9-OMe),7.14(m,2H,8-,10-H), 7.47-7.55(m,2H,3-,7-H),7.79 (dd,1H,J=5.2,9.2 Hz,4-H),8.09(dd,1H,J=2.8,9.6 Hz,1-H). $^{13}$C—NMR(100 MHz,DMSO-$d_6$):45.58 (2C), 50.97 (2C), 56.29, 106.78 (J=22.7 Hz), 111.47, 119.53, 119.82 (J=25.8 Hz), 120.73 (J=8.6 Hz), 125.40, 126.84, 130.75 (J=9.8 Hz), 133.74, 134.14, 134.86, 145.44, 157.14, 160.76 (J=244.1 Hz), 161.07, 194.46. Anal. calcd for $C_{21}H_{18}FN_3O_2 \cdot 0.3\ HCl$: C 67.39, H 4.93, N 11.23; found: C 67.34, H 5.26, N 11.12.

Synthesis Ex. 15

2-Chloro-9,10-dimethoxy-6-(piperazin-1-yl)-11H-indeno[1,2-c]quinolin-11-one (5ff)

2-Chloro-9,10-dimethoxy-6-(piperazin-1-yl)-11H-indeno[1,2-c]quinolin-11-one (5ff) was prepared substantially according to the procedures as set forth in the above Synthesis Example 12, except that compound 4g as obtained from the above Synthesis Example 5 was used in place of compound 4b. Compound 5ff was recrystallized from EtOH at a yield of 72%.

Detected Properties of the Title Compound:
M.p.:168-169° C. $^1$H—NMR(400 MHz,CDCl$_3$):3.14(m, 4H,piperazinyl-H), 3.36(m,4H,piperazinyl-H),3.91,4.14 (two s,6H,9-,10-OMe),6.89(d,1H,J=8.0 Hz,7-H),7.37(d,1H, J=8.0 Hz,8-H),7.48(dd,1H,J=2.4,9.2 Hz, 3-H),7.75(d,1H, J=8.8 Hz,4-H),8.74(d,1H,J=2.4 Hz,1-H). $^{13}$C—NMR (100 MHz,CDCl$_3$):45.85(2C), 50.98 (2C), 56.40, 62.33, 107.40, 115.85, 118.85, 121.41, 122.66, 129.21, 130.16, 132.40, 132.65, 134.80, 135.49, 146.72, 149.76, 154.37, 157.26, 191.99. Anal. calcd for $C_{22}H_{20}ClN_3O_3 \cdot 0.4\ H_2O$: C 63.34, H 5.04, N 10.07; found: C 63.08, H 5.33, N 9.82.

Synthesis Ex. 16

6-[4-(3-Chloropropanoyl)piperazin-1-yl]-9-methoxy-11H-indeno[1,2-c]quinolin-11-one (5hh)

A mixture of compound 5x (0.35 g, 1 mmol) as obtained from the above Synthesis Example 12, 3-chloropropanoyl chloride (0.65 g, 5 mmol), Et$_3$N (1 mL) and acetone (20 mL)

was stirred overnight at room temperature. After removal of solvent in vacuo, the residue was poured into saturated NaHCO$_{3(aq)}$ (50 mL). The resultant precipitate was collected by filtration, washed with H$_2$O, and dried to give a crude solid, which was purified by recrystallization from EtOH to give the title compound 5hh as a red solid (0.34 g, 78% yield).

Detected Properties of the Title Compound:
M.p.:162-163° C. $^1$H—NMR(400 MHz,CDCl$_3$):2.91(t, 2H,J=7.2 Hz,CH$_2$Cl), 3.36(m,2H,piperazinyl-H),3.49(m,2H, piperazinyl-H),3.76(m,2H, piperazinyl-H),3.87-3.90(m,7H, piperazinyl-H,COCH$_2$, and 9-OMe),6.95(dd,1H,J=2.4,8.0 Hz,8-H),7.24(d,1H,J=2.4 Hz,10-H),7.46(m,1H, 2-H),7.51(d, 1H,J=8.0 Hz,7-H),7.58(m,1H,3-H),7.82(d,1H,J=8.4 Hz, 4-H),8.70(d,1H,J=8.0 Hz,1-H). $^{13}$C—NMR(100 MHz, CDCl$_3$):36.08, 39.92, 41.52, 45.28, 49.49, 49.91, 55.84, 111.11, 118.95, 121.21, 123.80, 124.03, 127.31, 128.03, 129.68, 132.58, 134.83, 135.18, 136.22, 148.50, 156.28, 160.89, 168.49, 194.96. Anal. calcd for C$_{24}$H$_{22}$ClN$_3$O$_3$: C 66.13, H 5.09, N 9.64; found: C 66.02, H 5.09, N 9.56.

Synthesis Ex. 17

6-{4-{3-[2-(Dimethylamino)ethylamino] propanoyl}piperazin-1-yl}-9-methoxy-11H-indeno [1,2-c]quinolin-11-one (5bbb)

A mixture of compound 5hh (0.44 g, 1 mmol) as obtained in the above Synthesis Example 16, 2-(dimethylamino)ethylamine (0.44 g, 5 mmol) and ethanol (20 mL) was heated with stirring under microwave irradiation (150 W) for 30 min (by TLC monitoring). After removal of solvent in vacuo, the residue was poured into H$_2$O (50 mL). The resultant precipitate was collected by filtration, washed with H$_2$O, and dried to give a crude solid, which was purified by recrystallization from MeOH to give the title compound 5bbb as a red solid (0.35 g, 72% yield).

Detected Properties of the Title Compound:
M.p.:161-162° C. $^1$H—NMR(400 MHz,CDCl$_3$):2.24(s, 6H,N(CH$_3$)$_2$),2.43, 2.75(A$_2$B$_2$,4H,NCH$_2$CH$_2$N),2.64,2.97 (A$_2$B$_2$,4H,C(=O)CH$_2$CH$_2$N), 3.35(m, 2H,piperazinyl-H), 3.46(m,2H,piperazinyl-H),3.76(m,2H,piperazinyl-H), 3.88-3.91(m,5H,piperazinyl-H and OMe),6.96(dd,1H,J=2.4,8.0 Hz,8-H),7.24(d,1H,J=2.4 Hz,10-H),7.47(m,1H,2-H),7.53(d, 1H,J=8.0 Hz,7-H), 7.58(m,1H,3-H),7.83(dd,1H,J=1.2,8.4 Hz,4-H),8.71(dd,1H,J=1.2, 8.0 Hz,1-H). $^{13}$C—NMR(100 MHz,CDCl$_3$):33.59, 41.31, 45.18, 45.48, 45.62 (2C), 47.63, 49.53, 49.56, 55.84, 59.22, 111.12, 118.95, 121.19, 123.80, 124.09, 127.26, 128.04, 129.65, 132.65, 134.91, 135.20, 136.21, 148.55, 156.43, 160.89, 170.65, 195.02. ESIMS [M+H]$^+$: 488.

Synthesis Ex. 18

9-methoxy-6-[4-(oxiran-2-ylmethyl)piperazin-1-yl]-11H-indeno[1,2-c]quinolin-11-one (5kkk)

To a solution of compound 5x (0.35 g, 1 mmol, obtained from the above Synthesis Example 12) in dry DMF (20 mL) was added NaH (60% in oil, 2.64 g, 66.0 mmol) at 0° C. for 1 hr. After stirring at room temperature for 8 hrs, epichlorohydrin (0.92 g, 10 mmol) was added and stirred for a further 1 hr. The reaction mixture was partitioned between H$_2$O and CH$_2$Cl$_2$. The organic layer was dried over MgSO$_4$ and concentrated. The resultant residue was purified by column chromatography (MeOH/CH$_2$Cl$_2$=1:10) to give the title compound 5kkk (0.33 g, 84% yield).

Detected Properties of the Title Compound:
M.p.:138-139° C. $^1$H—NMR(400 MHz,CDCl$_3$):2.38(dd, 1H,J=7.8,13.2 Hz, OCH$_2$),2.56(dd,1H,J=2.8,5.2 Hz,oxiranyl-H),2.81(m,4H,piperazinyl-H), 2.84(dd,1H,J=4.4,5.2 Hz,oxiranyl-H),2.94(dd,1H,J=2.8,13.2 Hz, OCH$_2$),3.20(m, 1H,oxiranyl-H),3.45(m,4H,piperazinyl-H),3.87(s,3H, OMe),6.94(dd,1H,J=2.4,8.4 Hz,8-H),7.20(d,1H,J=2.4 Hz,10-H),7.43(m,1H,2-H),7.54(m,2H,3,7-H),7.83(d,1H, J=7.6 Hz,4-H),8.68(dd,1H, J=1.6,8.0 Hz,1-H). $^{13}$C—NMR (100 MHz,CDCl$_3$):44.78 (2C), 49.51 (2C), 50.36, 53.51, 55.75, 61.14, 110.84, 118.78, 120.91, 123.69, 124.34, 126.79, 127.95, 129.39, 132.71, 135.09, 135.17, 148.59, 156.84, 160.63, 195.22.
Anal. calcd for C$_{24}$H$_{23}$N$_3$O$_3$·0.25 H$_2$O: C 70.99, H 5.85, N 10.35; found: C 70.69, H 5.74, N 10.23.

Synthesis Ex. 19

6-{4-[2-Hydroxy-3-(methylamino)propyl]piperazin-1-yl}-9-methoxy-11H-indeno[1,2-c]quinolin-11-one (5lll)

A mixture of compound 5kkk (0.40 g, 1 mmol) as obtained from the above Synthesis Example 18, methylamine (40%, 5 mL) and EtOH (20 mL) was heated with stirring under microwave irradiation (100 W) for 30 min (by TLC monitoring). After removal of solvent in vacuo, the residue was poured into H$_2$O (50 mL). The resultant precipitate was collected by filtration, washed with H$_2$O, and dried to give a crude solid, which was purified by column chromatography (MeOH/CH$_2$Cl$_2$=1:5) to give the title compound 5lll as a viscous liquid (0.29 g, 67% yield).

Detected Properties of the Title Compound:
$^1$H—NMR(400 MHz,CDCl$_3$):2.47(s,3H,NMe),2.53-2.61 (m,2H,NCH$_2$), 2.67-2.71(m,2H,NCH$_2$),2.89,3.37(two m,8H,piperazinyl-H),3.82(s,3H, OMe),3.95(m,1H,CHO), 6.87(dd,1H,J=2.4,8.4 Hz,8-H),7.12(d,1H,J=2.4 Hz,10-H), 7.39(m,1H,2-H),7.44(d,1H,J=8.4 Hz,7-H),7.51(m,2H,3, 7-H),7.77(d,1H,J=8.4 Hz,4-H),8.62(d,1H,J=8.4 Hz,1-H). $^{13}$C—NMR (100 MHz,CDCl$_3$):36.38, 49.44, 49.56 (2C), 53.18, 55.62 (2C), 62.11, 65.63, 110.70, 118.59, 120.81, 123.58, 124.16, 126.71, 127.80, 129.27, 132.56, 134.91, 135.73, 148.42, 156.68, 160.50, 194.93. ESIMS [M+H]$^+$: 433.

Synthesis Ex. 20

9-Methoxy-11H-indeno[1,2-c]quinolin-11-one oxime (6a)

To a suspension of compound 5d (0.26 g, 1 mmol) in ethoxyethanol (30 mL) was added NH$_2$OH·HCl (0.20 g, 3 mmol). The reaction mixture was heated with stirring under microwave irradiation (100 W) for 30 min (by TLC monitoring), followed by concentration in vacuo. A solid thus obtained was recrystallized from MeOH to give the title compound 6a (0.20 g, 73% yield).

Detected Properties of the Title Compound:
M.p.: 270-271° C. $^1$H—NMR(400 MHz,CDCl$_3$):3.84(s, 3H,9-OMe),7.13(dd, 1H,J=2.84,8.4 Hz,8-H),7.84(m,2H,3, 10-H),7.93(m,1H,2-H),8.04(d, 1H,J=8.4 Hz,7-H),8.28(d, 1H,J=8.4 Hz,4-H),8.84(d,1H,J=8.4 Hz, 1-H),9.68(s,1H,6-H),14.24(br s,1H,NOH). $^{13}$C—NMR(100 MHz,CDCl$_3$): 55.65, 114.35, 116.54, 122.73, 126.36, 123.83, 125.69, 128.68, 130.09, 130.51, 131.75, 133.49, 139.04, 140.19, 141.42, 152.90, 160.97. Anal. calc. for $C_{17}H_{12}N_2O_2 \cdot 0.9H_2O \cdot 0.7HCl$; C 64.19, H 4.38, N 8.81; found: C 63.91, H 4.38, N 8.81.

Synthesis Ex. 21

6-Hydroxy-9-methoxy-11H-indeno[1,2-c]quinolin-11-one oxime (6c)

6-Hydroxy-9-methoxy-11H-indeno[1,2-c]quinolin-11-one oxime (6c) was prepared substantially according to the procedures as set forth in the above Synthesis Example 20, except that compound 5e was used in place of compound 5d. Compound 6c was recrystallized from EtOH at a yield of 82%.

Detected Properties of the Title Compound;

M.p.:320-321° C. $^1$H—NMR(400 MHz,CDCl$_3$):3.82(s, 3H,9-OMe),7.03 (dd, 1H,J=2.4,8.4 Hz,8-H),7.23(m,1H,3-H),7.39(dd,1H,J=1.2,8.4 Hz, 4-H),7.47(m,1H,2-H),7.89(d, 1H,J=2.4 Hz,10-H),8.03(d,1H,J=8.4 Hz, 7-H),8.56(dd,1H, J=1.6,8.0 Hz,1-H),12.00(br s,1H,6-OH),13.62(br s, 1H,NOH). $^{13}$C—NMR(100 MHz,CDCl$_3$):55.54, 114.95, 115.04, 115.91, 115.93, 122.50, 123.37, 125.44, 129.40, 129.45, 129.94, 131.02, 137.91, 138.82, 154.07, 158.79, 159.76. Anal. calc. for $C_{17}H_{12}N_2O_3 \cdot 0.2\ H_2O$: C 69.00, H 4.23, N 9.47; found: C 69.03, H 4.41, N 9.09.

Synthesis Ex. 22

6-(Piperazin-1-yl)-11H-indeno[1,2-c]quinolin-11-one O-methyl oxime (6j)

To a suspension of compound 5aa (0.32 g, 1 mmol) in ethoxyethanol (20 mL) was added NH$_2$OCH$_3$·HCl (0.42 g, 5 mmol). The reaction mixture was heated with stirring under microwave irradiation (150 W) for 30 min (by TLC monitoring), followed by concentration in vacuo. A solid thus obtained was recrystallized from MeOH to give the title compound 6j (0.29 g, 83% yield).

Detected Properties of the Title Compound:

M.p.:149-150° C. $^1$H—NMR(400 MHz,DMSO-d$_6$):3.43 (m,4H,piperazinyl-H), 3.52(m,4H,piperazinyl-H),4.36(s,3H, NOMe),7.43(m,1H,9-H),7.53(m, 1H,2-H),7.59(m,1H,8-H), 7.68(m,1H,3-H),7.82-7.92(m,2H,7-,10-H), 7.28(d,1H,J=6.8 Hz,4-H),8.79(dd,1H,J=0.8,8.4 Hz, 1-H). $^{13}$C—NMR (100 MHz,DMSO-d$_6$):42.52 (2C), 46.88 (2C), 64.56, 120.95, 122.98, 125.29, 126.36, 126.52, 128.30, 128.67, 128.75, 128.82, 129.70, 131.90, 138.13, 139.24, 146.79, 153.67, 156.05. Anal. calcd for $C_{21}H_{20}N_4O \cdot 1.1HCl$: C 65.60, H 5.53, N 14.57; found: C 65.81, H 5.53, N 14.61.

Synthesis Ex. 23

3-[2-(Dimethylamino)ethylamino]-1-{4-[11-hydroxyimino)-9-methoxy-11H-indeno[1,2-c]quinolin-6-yl]piparazin-1-yl}propan-1-one (6n)

3-[2-(Dimethylamino)ethylamino]-1-{4-[11-(hydroxyimino)-9-methoxy-11H-indeno[1,2-c]quinolin-6-yl]piperazin-1-yl}propan-1-one (6n) was prepared substantially according to the procedures as set forth in the above Synthesis Example 20, except that compound 5bbb was used in place of compound 5d. Compound 6n was recrystallized from EtOH at a yield of 42%.

Detected Properties of the Title Compound:

M-p.:146-147° C. $^1$H—NMR(400 MHz,CDCl$_3$):2.38(s, 6H,NMe$_2$),2.68 (m,6H, NCH$_2$,piperazinyl-H),2.97(m,2H, NCH$_2$),2.09(m,6H,NCH$_2$),3.24(m,6H, NCH$_2$,piperazinyl-H),3.88(s,3H, OMe),6.81(dd,1H,J=2.4,8 4 Hz,8-H), 7.42(m, 2H,2, 4-H),7.51(m,1H,3-H),7.73(d,1H,J=8.4 Hz,7-H),8.17 (d, 1H,J=2.4 Hz,10-H),8.80(d,1H,J=7.6 Hz,1-H). $^{13}$C—NMR(100 MHz, CDCl$_3$):44.91, 45.04(2C), 45.43 (2C), 46.82 (2C), 48.78, 49.40, 55.67, 58.21, 115.06, 115.21, 121.72, 122.77, 125.44, 125.74, 126.35, 128.40, 128.62, 130.98, 131.26, 139.71, 146.74, 154.34, 156.12, 159.84, 169.78. ESIMS [M+H]$^+$: 503.

Synthesis Ex. 24

9-Methoxy-6-(piperazin-1-yl)-11H-indeno[1,2-c]quinolin-11-one oxime (6p)

9-Methoxy-6-(piperazin-1-yl)-11H-indeno[1,2-c]quinolin-11-one oxime (6p) was prepared substantially according to the procedures as set forth in the above Synthesis Example 20, except that compound 5x was used in place of compound 5d. Compound 6p was recrystallized from EtOH at a yield of 81%.

Detected Properties of the Title Compound: M.p.:146-147° C. $^1$H—NMR(400 MHz,CDCl$_3$):2.06(m,4H,piperazinyl-H), 3.24(m,4H,piperazinyl-H),3.84(s,3H,OMe),7.13(d,1H, J=7.2 Hz,8-H), 7.46(m,1H,2-H),7.59(m,1H,3-H),7.80(m, 2H,4-, 7-H),8.02(s,1H,10-H), 8.76(d,1H,J=8.0 Hz,1-H). $^{13}$C—NMR(100 MHz,CDCl$_3$):44.91 (2C), 50.15 (2C), 55.52, 115.04, 115.32, 120.99, 123.56, 125.03, 125.66, 126.39, 128.14, 128.70, 130.18, 130.52, 138.82, 146.37, 153.66, 156.94, 159.60. ESIMS [M+H]$^+$: 361.

Synthesis Ex. 25

9-Methoxy-6-(piperazin-1-yl)-11H-indeno[1,2-c]quinolin-11-one O-2-(dimethylamino)ethyl oxime (6r)

9-Methoxy-6-(piperazin-1-yl)-11H-indeno[1,2-c]quinolin-11-one O-2-(dimethylamino)ethyl oxime (6r) was prepared substantially according to the procedures as set forth in the above Synthesis Example 18, except that compound 6p and 2-dimethylaminoethyl chloride·HCl were used in place of compound 5x and epichlorohydrin, respectively, giving the title compound at a yield of 45%.

Detected Properties of the Title Compound:

M.p.:84-86° C. $^1$H—NMR(400 MHz,CDCl$_3$):2.39(s,6H, NMe$_2$),2.89(t,2H,J=6.0 Hz,NCH$_2$),3.19(m,4H,piperazinyl-H),3.47(m,4H, piperazinyl-H), 3.88(s,3H,OMe),4.68(t,2H, J=6.0 Hz,NCH$_2$),6.95(dd,1H,J=2.4,8.4 Hz,8-H),7.41(m,1H, 2-H),7.55(m,1H,3-H),7.76(d,1H,J=8.4 Hz,7-H), 7.87(d,1H, J=8.4 Hz,4-H),7.98(d,1H,J=2.4 Hz,10-H),8.79(dd,1H,J=1.2, 8.4 Hz,1-H). $^{13}$C—NMR(100 MHz,CDCl$_3$)45.73(2C), 46.01 (2C), 50.78 (2C), 55.58, 58.20, 74.97, 115.23, 115.86, 121.67, 123.34, 125.48, 125.67, 127.40, 128.39, 128.53, 131.26, 132.12, 139.20, 147.18, 154.46, 157.09, 159.78. Anal. calcd for $C_{25}H_{29}N_5O_2 \cdot 0.4\ H_2O$: C 68.44, H 6.85, N 15.96; found: C 68.67, H 6.91, N 15.60.

Synthesis Ex. 26

9-Methoxy-6-(piperazin-1-yl)-11H-indeno[1,2-c]quinolin-11-one O-3-dimethylamino)propyl oxime (6s)

9-Methoxy-6-(piperazin-1-yl)-11H-indeno[1,2-c]quinolin-11-one O-3-(dimethylamino)propyl oxime (6s) was prepared substantially according to the procedures as set forth in the above Synthesis Example 18, except that compound 6p and 3-dimethylaminopropyl chloride·HCl were used in place of compound 5x and epichlorohydrin, respectively, giving the title compound at a yield of 52%.

Detected Properties of the Title Compound:
M.p.:145-146° C. $^1$H—NMR(400 MHz,CDCl$_3$):2.14 (quin, 2H,J=6.4 Hz, NCH$_2$CH$_2$CH$_2$N),2.33(s,6H,NMe$_2$), 2.59(t,2H,J=6.4 Hz,NCH$_2$),3.29(m, 4H,piperazinyl-H),3.44 (m,4H,piperazinyl-H),3.88(s,3H,OMe),4.62(t,2H, J=6.4 Hz,NCH$_2$),6.95(dd,1H,J=2.8,8.4 Hz,8-H),7.41(m,1H,2-H), 7.55(m,1H,3-H),7.80(d,1H,J=8.4 Hz,7-H),7.86(d,1H,J=8.0 Hz,4-H),7.92(d,1H,J=2.8 Hz,10-H),8.78(dd,1H,J=1.2,8.4 Hz,1-H). $^{13}$C—NMR(100 MHz,CDCl$_3$):27.28, 44.68 (2C), 45.49 (2C), 50.41 (2C), 55.58, 56.24, 74.81, 115.01, 115.97, 121.69, 123.15, 125.45, 125.67, 127.09, 128.30, 128.64, 131.16, 131.73, 139.37, 146.96, 154.11, 156.30, 159.82. ESIMS [M+H]$^+$: 446.

Synthesis Ex. 27

9-Methoxy-6-(piperazin-1-yl)-11H-indeno[1,2-c]quinolin-11-one O-3-aminopropyl oxime (6t)

9-Methoxy6-(piperazin-1-yl)-11H-indeno[1,2-c]quinolin-11-one O-3-aminopropyl oxime (6t) was prepared substantially according to the procedures as set forth in the above Synthesis Example 18, except that compound 6p and 3-bromopropylamine·Br were used in place of compound 5x and epichlorohydrin, respectively, giving the title compound at a yield of 41%.

Detected Properties of the Title Compound:
M.p.:89-90° C. $^1$H—NMR(400 MHz,DMSO-d$_6$):2.10 (quin,2H,J=6.4 Hz, NCH$_2$CH$_2$CH$_2$N),3.00(t,2H,J=6.4 Hz,NCH$_2$),3.15(m,4H,piperazinyl-H), 3.32(m,4H,piperazinyl-H),3.87(s,3H,OMe),4.67(t,2H,J=6.4 Hz,NCH$_2$), 7.18 (dd,1H,J=2.4,8.4 Hz,8-H),7.51(m,1H,2-H),7.63(m,1H,3-H), 7.78(d,1H,J=8.4 Hz,7-H),7.83(d,1H,J=8.4 Hz,4-H),7.87(d, 1H,J=2.4 Hz, 10-H),8.73(dd,1H,J=1.2,7.6 Hz,1-H). $^{13}$C—NMR(100 MHz,DMSO-d$_6$): 27.45, 36.07 (2C), 44.08, 49.14 (2C), 55.68, 73.47, 115.69, 115.90, 120.67, 123.93, 124.99, 126.19, 126.89, 128.24, 129.05, 130.28, 130.91, 138.09, 146.46, 153.92, 156.55, 159.74. ESIMS [M+H]$^+$: 418.

Synthesis Ex. 28

9-Methoxy-6-(piperazin-1-yl)-11H-indeno[1,2-c]quinolin-11-one O-2-(pyrrolidin-1-yl)ethyl oxime (6u)

9-Methoxy-6-(piperazin-1-yl)-11H-indeno[1,2-c]quinolin-11-one O-2-(pyrrolidin-1-yl)ethyl oxime (6u) was prepared substantially according to the procedures as set forth in the above Synthesis Example 18, except that compound 6p and 1-(2-chloroethyl)pyrrolidine·HCl were used in place of compound 5x and epichlorohydrin, respectively, giving the title compound at a yield of 43%.

Detected Properties of the Title Compound:
M.p.:126-128° C. $^1$H—NMR(400 MHz,DMSO-d$_6$):1.69 (m, 4H,pyrrolidinyl-H), 2.55(m,4H,pyrrolidinyl-H),2.94(t, 2H,J=5.6 Hz,NCH$_2$),2.95(m,4H, piperazinyl-H),3.21(m,4H, piperazinyl-H),3.83(s,3H,OMe),4.64(t,2H,J=5.6 Hz,NCH$_2$), 7.13(dd,1H,J=2.4,8.4 Hz,8-H),7.47(m,1H,2-H),7.60(m, 1H,3-H),7.75(d,1H,J=8.4 Hz,7-H),7.80(d,1H,J=8.4 Hz,4-H),7.89(d, 1H,J=2.4 Hz,10-H),8.70(dd,1H,J=1.2,8.4 Hz,1-H). $^{13}$C—NMR(100 MHz, DMSO-d$_6$):23.22 (2C), 45.08 (2C), 50.37 (2C), 54.08 (2C), 54.38, 55.50, 75.82, 115.48, 115.82, 120.85, 123.78, 124.97, 125.93, 126.87, 128.17, 128.90, 130.35, 131.01, 138.05, 146.54, 153.60, 156.95, 159.62. Anal. calcd for C$_{27}$H$_{31}$N$_5$O$_2$·0.4 H$_2$O: C 69.78, H 6.90, N 15.07; found: C 69.75, H 6.90, N 14.69.

Synthesis Ex. 29

9-Methoxy-6-(piperazin-1-yl)-11H-indeno[1,2-c]quinolin-11-one O-2-piperidin-1-yl)ethyl oxime (6v)

9-Methoxy-6-(piperazin-1-yl)-11H-indeno[1,2-c]quinolin-11-one O-2-(piperidin-1-yl)ethyl oxime (6v) was prepared substantially according to the procedures as set forth in the above Synthesis Example 18, except that compound 6p and 1-(2-chloroethyl)piperidine·HCl were used in place of compound 5x and epichlorohydrin, respectively, giving the title compound at a yield of 54%.

Detected Properties of the Title Compound:
M.p.:95-96° C. $^1$H—NMR(400 MHz,DMSO-d$_6$):1.38(m, 2H,piperidinyl-H), 1.51(m,4H,piperidinyl-H),2.51(m,4H,piperidinyl-H),2.81(t,2H,J=5.6 Hz, NCH$_2$),3.28(m,4H,piperazinyl-H),3.46(m,4H,piperazinyl-H),3.85(s,3H, OMe),4.66 (t,2H,J=5.6 Hz,NCH$_2$),7.15(dd,1H,J=2.8,8.4 Hz,8-H),7.48 (m,1H,2-H),7.61(m,1H,3-H),7.76(d,1H,J=8.4 Hz,7-H),7.81 (d,1H,J=8.4 Hz,4-H),7.2(d,1H,J=2.8 Hz,10-H),8.72(dd,1H, J=0.8,8.4 Hz, 1-H). $^{13}$C—NMR(100 MHz,DMSO-d$_6$):23.92, 25.62 (2C), 44.60 (2C), 49.70 (2C), 54.31 (2C), 55.54, 57.41, 74.44, 115.55, 115.85, 120.87, 123.79, 124.98, 126.03, 126.81, 128.18, 128.95, 130.34, 130.91, 138.10, 146.47, 153.58, 156.70, 159.68. Anal. calcd for C$_{28}$H$_{33}$N$_5$O$_2$·0.1 H$_2$O: C 71.04, H 7.07, N 14.79; found: C 70.76, H 7.40, N 14.45.

Synthesis Ex. 30

9-methoxy-11H-indeno[1,2-c]quinolin-11-one O-2-(pyrrolidin-1-yl)ethyl oxime (6aa)

9-methoxy-11H-indeno[1,2-c]quinolin-11-one O-2-(pyrrolidin-1-yl)ethyl oxime (6aa) was prepared substantially according to the procedures as set forth in the above Synthesis Example 18, except that compound 6a and 1-(2-chloroethyl)pyrrolidine·HCl were used in place of compound 5x and epichlorohydrin, respectively, giving the title compound at a yield of 56%.

Detected Properties of the Title Compound:
M.p.:85-86° C. $^1$H—NMR(400 MHz,CDCl$_3$):1.82(m,4H, pyrrolidinyl-H),2.69(m,4H,pyrrolidinyl-H),3.06(t,2H,J=6.0 Hz,NCH$_2$),3.86(s,3H,OMe), 4.72(t,2H,J=6.0 Hz,NCH$_2$), 6.94(dd,1H,J=2.4,8.4 Hz,8-H),7.55(m, 1H,2-H),7.62(m,2H, 3,7-H),7.91(d,1H,J=2.4 Hz, 10-H),8.06 (dd,1H,J=1.2,8.4 Hz,4-H),8.80(dd,1H,J=1.6,8.4 Hz,1-H),9.12(s,1H,6H). $^{13}$C—NMR(100 MHz,CDCl$_3$):23.52 (2C), 54.81 (2C), 54.89, 55.62, 76.05, 115.84, 116.00, 120.56, 123.89, 125.67, 128.10, 128.51, 130.06, 131.45, 131.80, 133.55, 136.45, 142.86, 148.13, 154.20, 160.44. Anal. calc. for C$_{23}$H$_{23}$N$_3$O$_2$·0.5 EtOH·0.1 HCl: C 72.03, H 6.59, N 10.50; found: C 72.05, H 6.33, N 10.30.

Synthesis Ex. 31

6-hydroxy-9-methoxy-11H-indeno[1,2-c]quinolin-11-one O-2-(pyrrolidin-1-yl)ethyl oxime (6bb)

6-Hydroxy-9-methoxy-11H-indeno[1,2-c]quinolin-11-one O-2-pyrrolidin-1-yl)ethyl oxime (6bb) was prepared substantially according to the procedures as set forth in the above Synthesis Example 18, except that compound 6c and 1-(2-chloroethyl)pyrrolidine·HCl were used in place of compound 5x and epichlorohydrin, respectively, giving the title compound at a yield of 46%.

Pharmacological Examples

In order to determine the biological activities of the compounds according to this invention, the following in vitro anticancer assay was performed.

In Vitro Anticancer Assay

Six cancer cells, i.e., cells of human cervical epithelioid carcinoma (HeLa), hepatocellular carcinoma (SKHep1), oral squamous cell carcinoma (SAS), human stomach adenocarcinoma (AGS), human renal clear cell carcinoma (RCC 768-O) and esophageal carcinoma (CE81T), were treated with the selected compounds as indicated for 48 hrs in a medium containing 10% FBS (3-[4,5-Dimethylthiazol-2-yl]-2,5-diphenyltetrazolium bromide (MTT, 2 mg/mL, 20 mL) was added to the cultures and incubated during the final 1.5 hrs. The resultant tetrazolium salt was then dissolved by the addition of dimethyl sulfoxide. Color was measured spectrophotometrically in a microtiter plate reader at 570 nm and used as a relative measure of viable cell number. The number of viable cells after treatment was compared to solvent and untreated control cells and used to determine the percent of control growth as $(Ab_{treated}/Ab_{control}) \times 100$, where Ab represents the mean absorbance (n=3). The concentration that killed 50% of cells ($IC_{50}$) was determined from the linear portion of the curve by calculating the concentration of agent that reduced absorbance in treated cells, as compared to control cells, by 50% (S. D. Heo et al. (1990), *Cancer Res.*, 50:3681-3690). (+)-camptothecin (CPT) and doxorubicin hydrochloride (Dox) were used for comparison with the compounds according to this invention. The obtained results are summarized in the following Table 2.

TABLE 2

Anti-proliferative evaluation of selected compounds ($IC_{50}$; μM)[a,b]

| Compd. | HeLa | SAS | SKHep1 | AGS | RCC 768-O | CE81T |
|---|---|---|---|---|---|---|
| 5a | 2.4 ± 1.2 | 6.6 ± 0.9 | 3.8 ± 1.8 | 7.9 ± 1.5 | 7.1 ± 0.6 | 4.1 ± 3.3 |
| 5b | 4.0 ± 0.9 | 6.9 ± 0.5 | 4.6 ± 1.5 | 9.8 ± 4.0 | 10.0 ± 0.8 | >30 |
| 5c | 1.0 ± 0.3 | 7.3 ± 0.6 | 4.3 ± 1.5 | 7.9 ± 1.7 | 8.3 ± 0.6 | >30 |
| 5i | 2.0 ± 0.4 | 5.5 ± 0.5 | 11.5 ± 5.4 | 14.3 ± 0.5 | >30 | 7.1 ± 0.3 |
| 5q | >30 | >30 | >30 | >30 | >30 | 22.7 ± 1.5 |
| 5s | 7.2 ± 0.9 | 6.5 ± 0.9 | 7.4 ± 2.1 | 5.9 ± 1.4 | 9.1 ± 1.5 | 6.8 ± 1.2 |
| 5v | >30 | >30 | 26.9 ± 19.5 | >30 | >30 | >30 |
| 5w | 1.1 ± 0.3 | 8.4 ± 2.6 | 2.6 ± 0.9 | 7.4 ± 0.6 | 5.3 ± 1.0 | 1.4 ± 0.7 |
| 5x | 15.2 ± 1.5 | >30 | 25.3 ± 15.5 | 10.1 ± 1.2 | 12.5 ± 1.0 | >30 |
| 5y | 3.4 ± 1.0 | 13.4 ± 2.6 | 2.9 ± 0.5 | 7.9 ± 1.2 | 13.6 ± 5.5 | 3.3 ± 2.2 |
| 5z | 3.0 ± 1.3 | 10.2 ± 2.5 | 6.2 ± 0.7 | 7.1 ± 1.1 | 10.2 ± 6.5 | 4.9 ± 1.3 |
| 5aa | 1.1 ± 0.6 | 10.7 ± 0.9 | 1.7 ± 1.1 | 6.5 ± 2.6 | 7.7 ± 0.4 | 11.1 ± 8.5 |
| 5bb | 0.4 ± 0.1 | 5.1 ± 0.8 | 0.7 ± 0.3 | 4.1 ± 1.2 | 1.7 ± 0.5 | 4.9 ± 1.5 |
| 5dd | 7.0 ± 1.2 | 11.7 ± 1.6 | 6.6 ± 3.2 | 7.4 ± 2.1 | 7.1 ± 0.6 | 8.3 ± 0.3 |
| 5ee | >30 | 6.9 ± 0.5 | 16.5 ± 5.1 | 6.5 ± 0.9 | 4.7 ± 3.0 | 0.9 ± 0.6 |
| 5ff | 4.6 ± 0.7 | 11.0 ± 3.2 | 4.7 ± 2.2 | 9.5 ± 2.7 | 6.9 ± 0.3 | >30 |
| 5kk | 2.0 ± 0.6 | 7.4 ± 0.9 | 4.8 ± 2.1 | 7.2 ± 1.5 | 6.2 ± 1.9 | 2.3 ± 1.3 |
| 5ll | 11.8 ± 2.8 | >30 | 19.2 ± 5.4 | 8.7 ± 1.2 | 14.1 ± 3.4 | >30 |
| 5mm | 8.7 ± 1.8 | >30 | 14.9 ± 3.6 | 11.2 ± 1.5 | 10.5 ± 1.0 | >30 |
| 5nn | 4.7 ± 2.3 | 11.3 ± 0.3 | 6.6 ± 0.9 | 6.5 ± 0.6 | 6.7 ± 0.5 | 9.2 ± 0.8 |
| 5oo | 8.2 ± 2.2 | 19.5 ± 3.2 | 16.0 ± 3.8 | 14.1 ± 2.3 | 9.4 ± 0.6 | >30 |
| 5pp | 10.8 ± 3.0 | >30 | 13.1 ± 2.7 | 5.6 ± 2.2 | 10.0 ± 2.1 | >30 |
| 5qq | >30 | >30 | >30 | 15.5 ± 1.5 | >30 | >30 |
| 5rr | 6.6 ± 1.3 | 8.6 ± 0.9 | 11.9 ± 2.5 | 3.5 ± 1.1 | 7.6 ± 0.1 | 6.6 ± 1.9 |
| 5ss | >30 | >30 | 21.5 ± 7.0 | 12.5 ± 5.2 | 10.8 ± 1.1 | >30 |
| 5tt | >30 | 7.4 ± 1.1 | 2.2 ± 1.3 | 3.4 ± 0.4 | 4.0 ± 1.5 | 7.2 ± 1.8 |
| 5uu | 18.0 ± 8.1 | >30 | 19.9 ± 10.0 | 21.4 ± 0.2 | >30 | >30 |
| 5vv | 5.4 ± 2.0 | 8.9 ± 0.1 | 6.4 ± 0.6 | 7.3 ± 0.1 | 5.6 ± 0.9 | 8.4 ± 2.0 |
| 5ww | 10.6 ± 1.6 | >30 | 21.9 ± 6.4 | 9.5 ± 0.3 | 18.5 ± 2.1 | >30 |
| 5xx | 1.9 ± 0.8 | 6.9 ± 0.7 | 9.1 ± 4.8 | 8.1 ± 1.1 | 6.0 ± 1.4 | 3.8 ± 0.6 |
| 5yy | 11.7 ± 1.7 | 17.0 ± 2.9 | 16.6 ± 2.0 | 8.1 ± 1.1 | 11.5 ± 1.8 | >30 |
| 5zz | 11.4 ± 0.4 | >30 | 19.0 ± 3.2 | 9.0 ± 2.0 | >30 | >30 |
| 5aaa | 3.1 ± 1.2 | 9.1 ± 1.6 | 4.5 ± 1.1 | 3.7 ± 0.5 | 2.0 ± 1.4 | 7.1 ± 0.9 |
| 5bbb | 4.8 ± 1.5 | 8.8 ± 1.0 | 5.1 ± 1.5 | 4.9 ± 1.0 | 7.0 ± 1.3 | 7.4 ± 2.0 |
| 5ccc | 5.4 ± 1.3 | 13.5 ± 2.2 | 8.6 ± 0.7 | 2.8 ± 1.3 | 5.9 ± 0.9 | 9.4 ± 0.6 |
| 5ddd | >30 | >30 | >30 | 10.8 ± 0.2 | >30 | >30 |
| 5eee | 10.6 ± 1.2 | >30 | 11.2 ± 0.9 | 16.0 ± 0.9 | 15.0 ± 3.5 | >30 |
| 5fff | >30 | >30 | 23.5 ± 1.4 | 10.8 ± 1.9 | >30 | >30 |
| 5ggg | 4.7 ± 1.4 | 7.7 ± 0.9 | 4.9 ± 1.1 | 5.5 ± 0.5 | 1.5 ± 1.3 | 7.2 ± 1.5 |
| 5hhh | 14.3 ± 4.4 | >30 | 15.0 ± 5.9 | 12.0 ± 1.3 | >30 | >30 |
| 5iii | >30 | >30 | 11.5 ± 5.6 | 13.4 ± 1.3 | >30 | >30 |
| 5jjj | 4.9 ± 1.7 | 8.0 ± 0.8 | 5.5 ± 0.8 | 5.4 ± 0.6 | 5.3 ± 0.5 | >30 |
| 5kkk | 10.7 ± 1.2 | >30 | >30 | 21.4 ± 10.1 | 19.1 ± 3.1 | 0.6 ± 2.1 |
| 5lll | 4.6 ± 1.0 | 7.4 ± 0.7 | 3.4 ± 1.2 | 9.6 ± 3.8 | 6.4 ± 0.2 | 0.9 ± 0.3 |
| 5mmm | 2.5 ± 0.7 | 6.9 ± 0.5 | 2.2 ± 0.8 | 7.9 ± 3.8 | 6.8 ± 0.1 | 4.8 ± 4.0 |
| 6e | 8.4 ± 1.2 | 9.5 ± 2.1 | 8.7 ± 2.1 | 6.8 ± 1.4 | >30 | >30 |

TABLE 2-continued

Anti-proliferative evaluation of selected compounds (IC$_{50}$; μM)$^{a,b}$

| Compd. | HeLa | SAS | SKHep1 | AGS | RCC 768-O | CE81T |
|---|---|---|---|---|---|---|
| 6i | 5.1 ± 0.6 | 7.3 ± 1.5 | 4.6 ± 1.1 | 7.6 ± 1.4 | 6.3 ± 1.3 | 3.5 ± 2.7 |
| 6j | 6.2 ± 0.6 | 7.7 ± 1.0 | 6.1 ± 0.8 | 8.1 ± 2.1 | 7.7 ± 0.5 | 0.4 ± 4.9 |
| 6k | 1.7 ± 0.2 | 4.4 ± 1.4 | 0.9 ± 0.3 | >30 | 2.3 ± 0.6 | 3.3 ± 1.8 |
| 6l | 4.9 ± 0.6 | 7.9 ± 0.3 | 5.9 ± 1.1 | 7.6 ± 3.4 | 7.0 ± 0.7 | 3.4 ± 0.3 |
| 6m | 3.6 ± 1.6 | 7.0 ± 0.5 | 5.0 ± 0.8 | 7.5 ± 1.1 | 5.3 ± 1.8 | 3.0 ± 2.0 |
| 6n | >30 | 7.3 ± 0.4 | >30 | 7.4 ± 1.2 | 5.6 ± 1.6 | >30 |
| 6o | 11.5 ± 1.3 | 19.1 ± 2.2 | 11.6 ± 7.3 | >30 | >30 | 4.8 ± 1.6 |
| 6p | 2.7 ± 1.2 | 6.1 ± 0.9 | 3.8 ± 1.3 | 1.7 ± 0.5 | 1.2 ± 0.9 | 2.6 ± 0.9 |
| 6q | 10.6 ± 4.4 | 10.3 ± 0.5 | 9.3 ± 2.9 | 5.2 ± 0.5 | 8.3 ± 1.3 | 7.2 ± 3.1 |
| 6r | 0.5 ± 0.2 | 2.4 ± 1.2 | 0.7 ± 0.2 | 6.8 ± 2.0 | 2.0 ± 1.9 | >30 |
| 6s | 0.6 ± 0.3 | 4.9 ± 0.6 | 3.0 ± 2.8 | 6.8 ± 1.8 | 4.9 ± 0.8 | >30 |
| 6t | 0.9 ± 0.4 | 6.3 ± 0.9 | 3.0 ± 2.2 | 5.9 ± 1.2 | 4.4 ± 1.4 | 6.5 ± 0.6 |
| 6u | 0.6 ± 0.2 | 2.4 ± 1.3 | 0.7 ± 0.3 | 4.8 ± 1.3 | 2.6 ± 0.5 | 2.9 ± 1.7 |
| 6v | 0.8 ± 0.3 | 5.8 ± 0.5 | 1.6 ± 0.5 | 7.1 ± 0.8 | 4.5 ± 1.4 | >30 |
| 6w | 0.8 ± 0.2 | 6.9 ± 1.3 | 1.0 ± 0.4 | 5.8 ± 1.9 | 4.1 ± 1.9 | >30 |
| 6x | 6.1 ± 0.3 | 7.6 ± 0.6 | 4.2 ± 1.8 | 6.1 ± 1.4 | 7.0 ± 0.4 | 3.4 ± 2.3 |
| 6y | 0.5 ± 0.2 | 6.2 ± 0.9 | 1.0 ± 0.5 | 8.8 ± 4.1 | 8.8 ± 2.2 | 2.0 ± 1.2 |
| 6z | 1.0 ± 0.4 | 9.0 ± 2.7 | 2.5 ± 1.7 | 18.6 ± 6.2 | 13.9 ± 10.5 | 9.0 ± 3.6 |
| 6aa | 0.4 ± 0.02 | 1.2 ± 0.2 | 1.5 ± 0.3 | >30 | 5.7 ± 1.0 | — |
| 6bb | 0.2 ± 0.02 | 0.8 ± 0.1 | 1.2 ± 0.3 | 10.4 ± 3.0 | 3.7 ± 0.8 | — |
| CPT$^c$ | 0.3 ± 0.1 | 6.0 ± 2.7 | 0.2 ± 0.1 | >30 | 2.8 ± 0.7 | 2.8 ± 1.5 |
| Dox$^c$ | 0.4 ± 0.1 | 5.7 ± 0.3 | <0.1 | >30 | 2.2 ± 0.3 | 0.3 ± 0.1 |

$^a$The concentration that killed 50% of cells (IC$_{50}$) was determined from the linear portion of the curve by calculating the concentration of agent that reduced absorbance in treated cells, as compared to control cells, by 50% (n = 4).
$^b$Tested cells are human cervical epithelioid carcinoma (HeLa), hepatocellular carcinoma (SKHep1), oral squamous cell carcinoma (SAS), human stomach adenocarcinoma (AGS), human renal clear cell carcinoma (RCC 768-O), and esophageal carcinoma (CE81T).
$^c$CPT, (+)-camptothecin; and Dox, doxorubicin hydrochloride.

Referring to Table 2, compounds of formula (1) according to this invention, especially compounds 6r-6z, and their synthetic precursors, such as compound 5bb, are shown to have a broad and potent anticancer activity. It is thus contemplated that compounds of formula (I) of this invention as well as their synthetic precursors can be used for the treatment of cancers, especially human cervical epithelioid carcinoma, hepatocellular carcinoma, and oral squamous cell carcinoma.

All patents and literature references cited in the present specification as well as the references described therein, are hereby incorporated by reference in their entirety. In case of conflict, the present description, including definitions, will prevail.

While the invention has been described in connection with specific embodiments thereof, it will be understood that it is capable of further modifications and this application is intended to cover any variations, uses, or adaptations of the invention following, in general, the principles of the invention and including such departures from the present customary practice within the art to which the invention pertains and as may be applied to the essential features hereinbefore set forth, and as follows in the scope of the appended claims.

We claim:
1. A compound of formula (I):

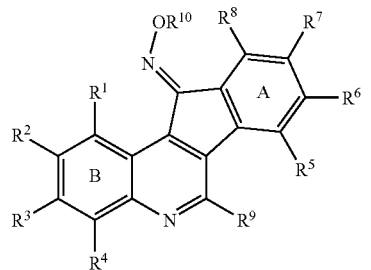

(I)

or a pharmaceutically acceptable salt thereof, wherein:
R$^1$, R$^2$, R$^3$ and R$^4$, which may be the same or different, independently represent:
(1) hydrogen, halogen, hydroxy, mercapto, cyano, nitro, —COOH, or —CONH$_2$;
(2) a group (i) selected from an amino group, a C$_1$-C$_{12}$ alkyl group, a C$_1$-C$_{12}$ alkoxy group, a C$_1$-C$_{12}$ alkoxycarbonyl group, a C$_1$-C$_{12}$ alkylthio group, a C$_1$-C$_{12}$ alkanoyl group, a C$_1$-C$_{12}$ alkanoyloxy group, a C$_2$-C$_{12}$ alkenyl group and a C$_2$-C$_{12}$ alkenyl group, the group (i) being unsubstituted or substituted with one to three substituents selected from the group consisting of halo, amino, cyano, hydroxy, mercapto, —COOH, —CF$_3$, —OCF$_3$, —SCF$_3$, —CONH$_2$, a C$_1$-C$_6$ alkoxy group, and an aryl group; or
(3) a group (ii) selected from phenyl, phenoxy, phenylthio, pyridyl, pyrrolidinyl, piperazinyl, piperidyl and diazepinyl, the group (ii) being unsubstituted or substituted with one to three substituents selected from the group consisting of halo, amino, cyano, hydroxy, mercapto, —COOH, —CF$_3$, —OCF$_3$, —SCF$_3$, —CONH$_2$, a C$_1$-C$_6$ alkyl group, a C$_1$-C$_6$ alkoxy group, and an aryl group;
R$^5$, R$^6$, R$^7$ and R$^8$, which may be the same or different, independently represent:
(1) hydrogen, halogen, hydroxy, mercapto, cyano, nitro, —COOH, or —CONH$_2$;
(2) a group (i) selected from an amino group, a C$_1$-C$_{12}$ alkyl group, a C$_1$-C$_{12}$ alkoxy group, a C$_1$-C$_{12}$ alkoxycarbonyl group, a C$_1$-C$_{12}$ alkylthio group, a C$_1$-C$_{12}$ alkanoyl group, a C$_1$-C$_{12}$ alkanoyloxy group, a C$_2$-C$_{12}$ alkenyl group and a C$_2$-C$_{12}$ alkenoyl group, the group (i) being unsubstituted or substituted with one to three substituents selected from the group consisting of halo, amino, cyano, hydroxy, mercapto, —COOH, —CF$_3$, —OCF$_3$, —SCF$_3$, —CONH$_2$, a C$_1$-C$_6$ alkoxy group, and an aryl group; or (3) a group (ii) selected from phenyl, phenoxy, phenylthio, pyridyl, pyrrolidinyl, piperazinyl, piperidyl and diazepinyl, the group (ii) being unsubstituted or substituted with one to three substituents selected from the group consisting of halo, amino, cyano, hydroxy, mercapto, —COOH, —CF$_3$, —OCF$_3$, —SCF$_3$, —CONH$_2$, a C$_1$-C$_6$ alkyl group, a C$_1$-C$_6$ alkoxy group, and an aryl group;

R$^9$ represents:
(1) hydrogen;
(2) halogen;
(3) hydroxy;
(4) a C$_1$-C$_6$ alkoxy group ;
(5) a C$_3$-C$_{10}$ monocyclic heterocyclic group containing from one to three heteroatoms selected from O, S and N, wherein the heterocyclic group is unsubstituted or substituted with one to three substituent groups selected from a C$_1$-C$_6$ alkyl group, a C$_1$-C$_6$ alkanoyl group, and a C$_1$-C$_{20}$ alkanoyl group interrupted by one or two amino groups of formula —NR'— where R' is hydrogen or (C$_1$-C$_6$)alkyl, each of the substituent groups being unsubstituted or substituted with one to three groups selected from halo, amino, cyano, hydroxy, mercapto, —COOH, —CONH$_2$, a C$_1$-C$_6$ alkyl group, a C$_1$-C$_6$ alkoxy group, a (C$_1$-C$_6$)alkylamino group, a (C$_1$-C$_6$)dialkylamino group, an aryl group, and a C$_3$-C$_6$ heterocyclic group containing one to two heteroatoms selected from O and N; or
(6) a group of formula —NHR, in which R represents: a C$_1$-C$_6$ alkyl group, a C$_1$-C$_{20}$ alkyl group interrupted by one or two amino groups of formula —NR'— where R' is hydrogen or (C$_1$-C$_6$)alkyl, or an aryl group, and wherein R is unsubstituted or substituted with one to three substituents selected from halo, amino, cyano, hydroxy, mercapto, —COOH, —CONH$_2$, a C$_1$-C$_6$ alkyl group, a C$_1$-C$_6$ alkoxy group, a C$_1$-C$_6$ alkanoyl group, a (C$_1$-C$_6$)alkylamino group, a (C$_1$-C$_6$)dialkylamino group, an aryl group, and a C$_3$-C$_6$ heterocyclic group containing one to two heteroatoms selected from O and N; and R$^{10}$ represents:
hydrogen; or
a group (iii) selected from a C$_1$-C$_6$ alkyl group, a C$_1$-C$_6$ aminoalkyl group, phenyl, the group (iii) being unsubstituted or substituted with one to three substituents selected from halo, amino, cyano, hydroxy, mercapto, —COOH, —CONH$_2$, a C$_1$-C$_6$ alkyl group, a C$_1$-C$_6$ alkoxy group, a C$_1$-C$_6$ aminoalkyl group, phenyl, and a C$_3$-C$_6$ heterocyclic group containing one to two heteroatoms selected from O and N.

2. The compound of claim 1, wherein R$^1$, R$^2$, R$^3$ and R$^4$ independently represent: hydrogen, fluoro, chloro, bromo, iodo, hydroxy, mercapto, cyano, amino, nitro, —COOH, —CONH$_2$, methyl, ethyl, propyl, isopropyl, n-butyl, t-butyl, n-pentyl, methoxy, ethoxy, propoxy, butoxy, methylthio, ethylthio, formyl, acetyl, propionyl, butyryl, acetoxy, propionyloxy, butyryloxy, phenylacetyl, hydroxymethyl, aminomethyl, aminoethyl, fluoromethyl, chloromethyl, bromomethyl, trifluoromethyl, trifluoromethoxy, trifluoromethylthio, methoxycarbonyl, ethoxycarbonyl, propoxycarbonyl, butoxycarbonyl, phenyl, phenoxy, 4-hydroxy-3-isopropylphenoxy, phenylthio, benzyl, benzoyl, benzyloxy, styryl, anilino, 2,6-dichioroanilino, or 3-methylbuten-2-yl.

3. The compound of claim 1, wherein R$^5$, R$^6$, R$^7$ and R$^8$ independently represent: hydrogen, fluoro, chloro, bromo, iodo, hydroxy, mercapto, cyano, amino, nitro, —COOH, —CONH$_2$, methyl, ethyl, propyl, isopropyl, n-butyl, t-butyl, n-pentyl, methoxy, ethoxy, propoxy, butoxy, methylthio, ethylthio, formyl, acetyl, propionyl, butyryl, acetoxy, propionyloxy, butyryloxy, phenylacetyl, hydroxymethyl, aminomethyl, aminoethyl, fluoromethyl, chloromethyl, bromomethyl, trifluoromethyl, trifluoromethoxy, trifluoromethylthio, methoxycarbonyl, ethoxycarbonyl, propoxycarbonyl, butoxycarbonyl, phenyl, phenoxy, phenylthio, benzyl, benzoyl, benzyloxy, styryl, anilino, 4-hydroxy-3-isopropylphenoxy, or 2,6-dichloroanilino.

4. The compound of claim 1, wherein R$^9$ is a C$_3$-C$_{10}$ monocyclic heterocyclic group selected from pyrrolyl, pyrrolinyl, pyrrolidinyl, pyrazolyl, pyrazolinyl, pyrazolidinyl, imidazolyl, triazolyl, oxazolyl, isoxazolyl, thiazolyl, isothiazolyl, pyridyl, piperidyl, pyridazinyl, pyrimidinyl, pyrazinyl, piperazinyl, morpholinyl, diazepinyl, thiazinyl, dioxanyl and uracilyl, the nitrogen-containing heterocyclic group being unsubstituted or substituted with one to three substituent groups selected from a C$_1$-C$_6$ alkyl group, a C$_1$-C$_6$ alkanoyl group, and a C$_1$-C$_{20}$ alkanoyl group interrupted by one or two amino groups of formula —NR'— where R' is hydrogen or (C$_1$-C$_6$)alkyl, each of the substituent groups being unsubstituted or substituted with one to three groups selected from halo, amino, cyano, hydroxy, mercapto, —COOH, —CONH$_2$, a C$_1$-C$_6$ alkyl group, a C$_1$-C$_6$ alkoxy group, a (C$_1$-C$_6$)alkylamino group, a (C$_1$-C$_6$)dialkylamino group, phenyl, oxiranyl, pyridyl, pyrrolidinyl, piperidyl, piperazinyl, diazepinyl, and morpholinyl.

5. The compound of claim 1, wherein R$^9$ is a group of formula —NHR, in which R represents: phenyl, a C$_1$-C$_6$ alkyl group, or a C$_1$-C$_{20}$ alkyl group interrupted by one or two amino groups of formula —NR'— where R' is hydrogen or (C$_1$-C$_6$)alkyl, and wherein R is unsubstituted or substituted with one to three substituents selected from halo, amino, cyano, hydroxy, mercapto, —COOH, —CONH$_2$, a C$_1$-C$_6$ alkyl group, a C$_1$-C$_6$ alkoxy group, a C$_1$-C$_6$ alkanoyl group, a (C$_1$-C$_6$) alkylamino group, a (C$_1$-C$_6$)dialkylamino group, phenyl, oxiranyl, pyridyl, pyrrolidinyl, piperidyl, piperazinyl, diazepinyl, and morpholinyl.

6. The compound of claim 1, wherein R$^9$ is selected from the group consisting of: hydrogen, chloro, hydroxyl, methoxy, ethoxy, methoxyamino, 2-ethoxyethylamino, 2-(2-hydroxyethylamino)ethylamino, 2-aminopyrrolidinyl, 2-acetylphenylamino, 2-(dimethylamino)ethylamino, 3-(dimethylamino)propylamino, 4-aminopiperidyl, 4-fluorophenylamino, 4-chlorophenylamino, 2,4-difluorophenylamino, 3,4-difluorophenylamino, 2,4-dichlorophenylamino, 1,4-diazepen-1-yl, 4-methoxyphenylamino,3-methoxyphenylamino, piperazin-1-yl, 2,4-dimethoxyphenylamino, 3,4-dimethoxyphenylamino, 4-acetylphenylamino, 3-acetylphenylamino, 3-methypiperazin-1-yl, 4-[(3-methylamino)propionyl]piperazin-1-yl, 4-(2-chloroacetyl)piperazin-1-yl, 4-(3-hydroxypropionyl)piperazin-1-yl, 4-(3-chloropropionyl)piperazin-1-yl, 4-(4-chlorobutyryl)piperazin-1-yl, 4-(2-hydroxyacetyl)piperazin-1-yl, 4-(2-methylaminoacetyl)piperazin-1-yl, 4-(2-dimethylaminoacetyl)piperazin-1-yl, 4-(4-dimethylaminobutyryl)piperazin-1-yl, 4-[(3-dimethylamino)propionyl]piperazin-1-yl, 4-[2-(2-aminoethyl)aminoacetyl]piperazin-1-yl, 4-[2-(2-hydroxyethyl)aminoacetyl]piperazin-1-yl, 4-[2-hydroxy-3-(methylamino)propyl]piperazin-1-yl, 4-[3-(2-hydroxyethylamino)propionyl]piperazin-1-yl, 4-[2-hydroxy-3-(dimethylamino)propyl]piperazin-1-yl, 4-{3-[2-(dimethylamino)ethylamino]propanoyl}piperazin-1-yl,

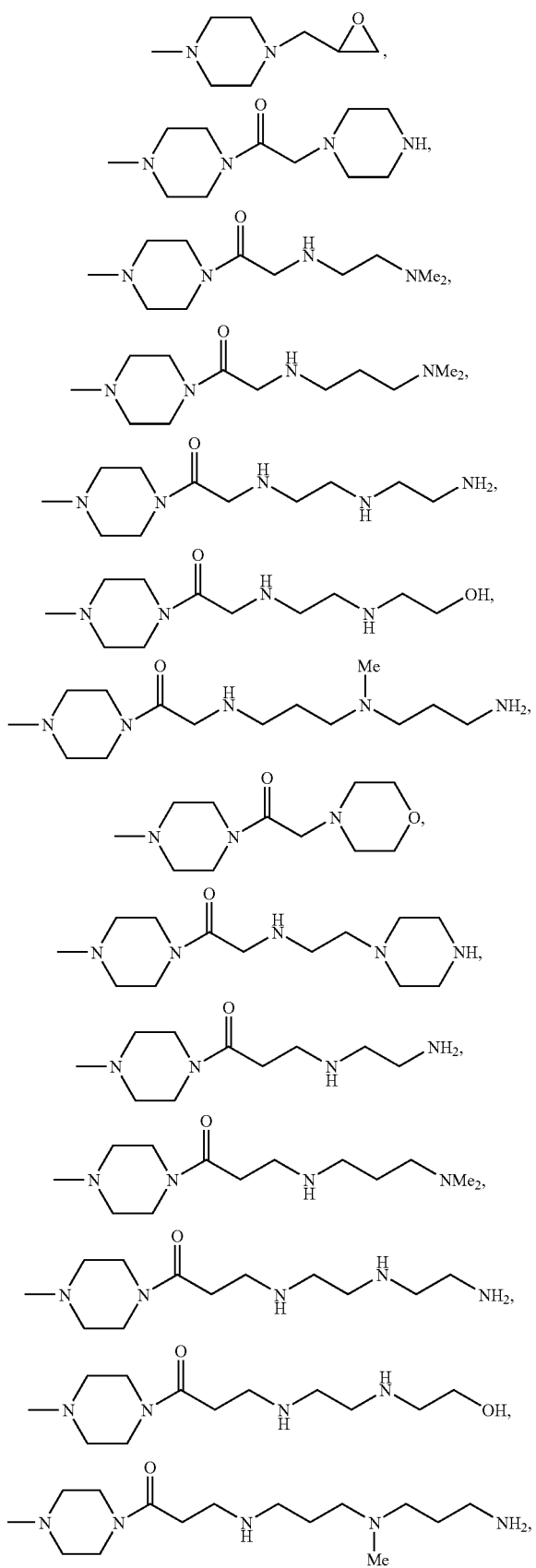

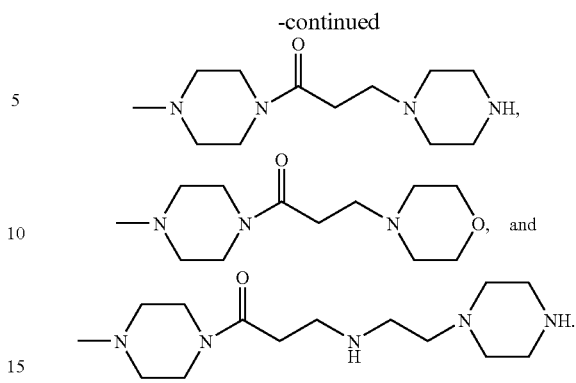

7. The compound of claim 1, wherein $R^{10}$ is selected from the group consisting of:

hydrogen; or a group (iii) selected from a $C_1$-$C_6$ alkyl group, a $C_1$-$C_6$ aminoalkyl group and phenyl, the group (iii) being unsubstituted or substituted with one to three substituents selected from halo, amino, cyano, hydroxy, mercapto, —COOH, —CONH$_2$, a $C_1$-$C_6$ alkyl group, a $C_1$-$C_6$ alkoxy group, a $C_1$-$C_6$ aminoalkyl group, phenyl, oxiranyl, pyridyl, pyrrolidinyl, piperidyl, piperazinyl, diazepinyl, and morpholinyl.

8. The compound of claim 1, wherein $R^{10}$ is selected from the group consisting of: hydrogen, methyl, benzyl, 2-(dimethylamino)ethyl, oxiran-2-ylmethyl, 3-aminopropyl, 2-hydroxy-3-(dimethylamino)propyl, 2-(pyrrolidin-1-yl)ethyl, 2-(piperidin-1-yl)ethyl, 3-(dimethylamino)propyl, and 2-(morpholin-1-yl)ethyl.

9. The compound of claim 1, which is selected from:

9-methoxy-11H-indeno[1,2-c]quinolin-11-one oxime;

6-hydroxy-9-methoxy-11H-indeno[1,2-c]quinolin-11-one oxime;

6-(Piperazin-1-yl)-11H-indeno[1,2-c]quinolin-11-one O-methyl oxime;

3-[2-(Dimethylamino)ethylamino]-1-{4-[11-(hydroxyimino)-9-methoxy-11H-indeno[1,2-c]quinolin-6-yl]piperazin-1-yl}propan-1-one;

9-Methoxy-6-(piperazin-1-yl)-11H-indeno[1,2-c]quinolin-11-one oxime;

9-Methoxy-6-(piperazin-1-yl)-11H-indeno[1,2-c]quinolin-11-one O-2-(dimethylamino)ethyl oxime;

9-Methoxy-6-(piperazin-1-yl)-11H-indeno[1,2-c]quinolin-11-one O-3-(dimethylamino)propyl oxime;

9-Methoxy-6-(piperazin-1-yl)-11H-indeno[1,2-c]quinolin-11-one O-3-aminopropyl oxime;

9-Methoxy-6-(piperazin-1-yl)-11H-indeno[1,2-c]quinolin-11-one O-2-(pyrrolidin-1-yl)ethyl oxime;

9-Methoxy-6-(piperazin-1-yl)-11H-indeno[1,2-c]quinolin-11-one O-2-(piperidin-1-yl)ethyl oxime;

9-methoxy-11H-indeno[1,2-c]quinolin-11-one O-2-(pyrrolidin-1-yl)ethyl oxime; and 6-hydroxy-9-methoxy-11H-indeno[1,2-c]quinolin-11-one O-2-(pyrrolidin-1-yl)ethyl oxime.

10. A process for preparing a compound of formula (I) or a pharmaceutically acceptable salt thereof as claimed in claim 1, comprising subjecting a compound of formula (II):

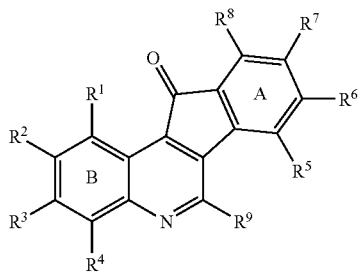

(II)

wherein the $R^1$-$R^9$ groups have the same definitions as those defined in claim 1, to a chemical treatment selected from:

(i) a reaction with $NH_2OH$, optionally followed by alkylation with an alkyl halide of formula $R^{10}X$, where $R^{10}$ has the same definition as that defined in claim 1, and X is a halogen; and (ii) a reaction with $NH_2OR^{10}$, where $R^{10}$ has the same definition as that defined in claim 1.

* * * * *